United States Patent [19]
Levy et al.

[11] Patent Number: 5,637,599
[45] Date of Patent: Jun. 10, 1997

[54] ARGININE MIMIC DERIVATIVES AS ENZYME INHIBITORS

[75] Inventors: Odile E. Levy; Susan Y. Tamura; Ruth F. Nutt; William C. Ripka, all of San Diego, Calif.

[73] Assignee: Corvas International, Inc., San Diego, Calif.

[21] Appl. No.: 261,478

[22] Filed: Jun. 17, 1994

[51] Int. Cl.$^6$ .................. A61K 31/445; C07D 401/12
[52] U.S. Cl. .................. 514/326; 514/316; 514/318; 546/191; 546/193; 546/208; 546/210
[58] Field of Search .................. 546/193, 191, 546/208, 210; 514/326, 316, 318

[56] References Cited

U.S. PATENT DOCUMENTS

| | | | |
|---|---|---|---|
| 4,316,889 | 2/1982 | Bajusz et al. | 514/326 |
| 4,433,152 | 2/1984 | Muramatsu et al. | 546/193 |
| 4,772,686 | 9/1988 | Szelke et al. | 530/331 |
| 5,053,392 | 10/1991 | Klein et al. | 514/18 |
| 5,196,404 | 3/1993 | Maraganore et al. | 514/13 |
| 5,260,307 | 11/1993 | Ackermann et al. | 514/323 |
| 5,314,902 | 5/1994 | Tjoeng et al. | 514/357 |
| 5,492,895 | 1/1996 | Vlasuk et al. | 514/18 |

FOREIGN PATENT DOCUMENTS

| | | | |
|---|---|---|---|
| 0526877 | 2/1993 | European Pat. Off. | 401/6 |
| 2490632 | 3/1982 | France | 103/52 |
| WO95/35312 | 12/1995 | WIPO | 5/6 |

OTHER PUBLICATIONS

Bagdy et al. "In vitro inhibition of blood coagulation by tripeptide aldehydes" CA 117:20172v (1992).

Tung et al. "Correlation of molecular shape with GPIIb-IIIa Receptor antagonist activity in RGD peptides" Receptor vol. 3, pp. 343–356 (1993).

Zablock et al. "Potent in vitro and in vivo inhibitors of platelet aggregation based upon the Arg-Gly-Asp-Phe sequence of fibrinogen". J. Med. Chem. vol. 36, pp. 1811–1819 (1993).

G. Wagner et al., *Pharmazie*, 39:5 pp. 315–317 (May 1984).

H. Vieweg et al., *Pharmazie*, 42:4 pp. 315–317 (Apr. 1987).

Banner, D.A. et al., Perspect. Med. Chem. 1993, pp. 27–43.

*Primary Examiner*—Ceila Chang
*Attorney, Agent, or Firm*—Lyon & Lyon LLP

[57] ABSTRACT

The present invention discloses peptide aldehydes which are potent and specific inhibitors of thrombin, their pharmaceutically acceptable salts, pharmaceutically acceptable compositions thereof, and methods of using them as therapeutic agents for disease slates in mammals characterized by abnormal thrombosis.

16 Claims, 3 Drawing Sheets log[2-PrPent-Asp(OMe)-Pro-Ala(3-guanPip)-al (Isomer B)]μM

ARGININE MIMIC DERIVATIVES AS ENZYME INHIBITORS

TECHNICAL FIELD

In one aspect, the present invention relates compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vive in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391 (1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

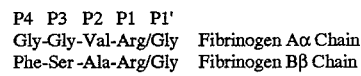

P4 P3 P2 P1 P1'
Gly-Gly-Val-Arg/Gly   Fibrinogen Aα Chain
Phe-Ser-Ala-Arg/Gly   Fibrinogen Bβ Chain Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 1990 and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-

L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombin by binding to both its anion-binding exo-site and to its catalytic active site which are distinct and physically distant from each other. Rydel, T. J. et al., Science, 249: 277 (1990). Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, L. W. et al., J. Biol. Chem., 266: 16977 (1991). Hirugen also is reported to block thrombin-mediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., Thromb. Res., 1: 243–52 (1972). Other benzamidine-derived structures which have been reported to inhibit thrombin include the cylic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., Thromb. Res., 17: 425–31 (1980). Moreover, derivatives of 4-amidinophenylalanine whose $\alpha$-amino group is linked to the arylsulfonyl residue via an $\omega$-aminoalkylcarboxylic acid as spacer have also been assessed for their inhibitory effect. Among these $N^\alpha$-(2-naphthylsulphonylglycyl)-4-amidino-phenylalanine piperidide ($\alpha$-NAPAP) has been reported to possess an affinity for thrombin ($K_i=6\times10^{-9}M$). Banner et al., J. Biol. Chem., 266: 20085 (1991) and Sturzebecher et al., Thromb. Res., 29: 635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et. al., Thromb. Diath. Haemorrh., 29: 154–67 (1973); Geratz et. al., J. Med. Chem., 16: 970–5 (1973); Geratz et. al., J. Med. Chem., 19: 634–9 (1976); Walsmann et. al., Acta Biol. Med. Germ., 35: K1–8 (1976); and Hauptmann et. al., Acta Biol. Med. Germ., 35: 635–44 (1976).

Certain amidino-bearing aromatic ring structures such a $\beta$-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., Biochim. Biophys. Acta, 661: 342–5 (1981); and Hitomi et. al., Haemostasis, 15: 164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et. al., Thromb. Haemostas., 50: 53 (1983). Another compound, [ethyl p-(6-guanidinohexanoyloxy) benzoate] methane sulfonate (FOY) was reported to be a non-selective competitive inhibitor of thrombin. Ohno et al., Thromb. Res., 19: 579–588 (1980).

SUMMARY OF THE INVENTION

The present invention is directed to novel compounds that are peptide aldehydes having arginine mimics in the $P_1$ position and which are potent inhibitors of thrombin in vivo and in vitro.

Thus, in one aspect, the present invention is directed to to compounds of the formula

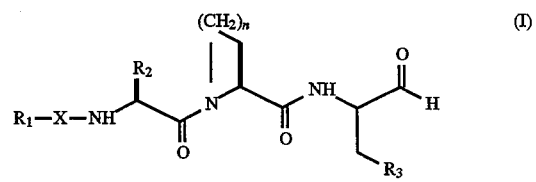

wherein (a) X is selected from the group consisting of —OC(=O)—, —NH—C(=O)—, —C(=O)—, —S(O)$_2$—, —NH—S(O)₂— and —N(R')—S(O)₂— wherein R' is alkyl of 1 to about 4 carbon atoms, aryl of about 6 to about 14 carbon atoms, or aralkyl of about 6 to about 15 carbon atoms;

(b) R₁ is selected from the group consisting of:
(1) alkyl of about 3 to about 10 carbon atoms,
(2) alkyl of 1 to about 3 carbon atoms substituted with cyclic alkyl of about 5 to about 8 carbon atoms,
(3) alkenyl of about 3 to about 6 carbon atoms which is optionally substituted with cyclic alkyl of about 5 to about 8 carbon atoms,
(4) aryl of about 6 to about 14 carbon atoms which is optionally mono-substituted with Y₁ or optionally di-substituted with Y₁ and Y₂,
(5) aralkyl of about 6 to about 15 carbon atoms which is optionally mono-substituted in the aryl ring with Y₁ or optionally di-substituted in the aryl ring with Y₁ and Y₂,
(6) aralkenyl of about 8 to about 15 carbon atoms which is optionally mono-substituted in the aryl ring with Y₁ or optionally di-substituted in the aryl ring with Y₁ and Y₂,

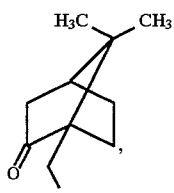
(7)

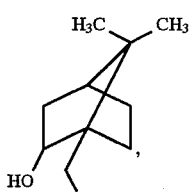
(8)

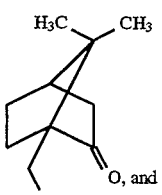
(9)

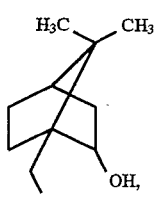
(10)

wherein Y₁ and Y₂ are independently selected from the group consisting of —Z₁, —OZ₁, —OH, —S(O)ₘZ₁, —S(O)₃H, —C(O)OH, —C(O)OZ₁, —P(O)₃H, and tetrazolyl where m is 0, 1 or 2 and Z₁ is alkyl of 1 to about 12 carbon atoms, aryl of about 6 to about 14 carbon atoms and an aralkyl of about 6 to about 15 carbon atoms;

(c) R₂ is selected from the group consisting of

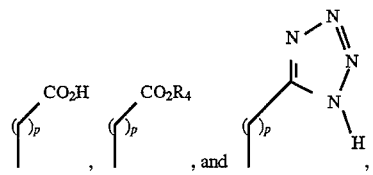

wherein p is 1 or 2 and R₄ is selected from the group consisting of alkyl of 1 to about 4 carbon groups, aryl of about 6 to about 15 carbon atoms;
(d) n is 1, 2 or 3;
(e) R₃ is selected from the group consisting of

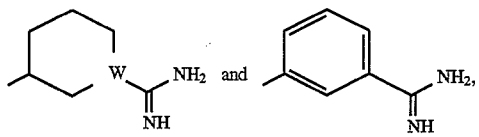

where W is nitrogen or carbon; and pharmaceutically acceptable salts thereof.

Among other factors, the present invention is based on our finding that the novel compounds are active as selective inhibitors of thrombin in vivo and in vitro. Furthermore, certain of the preferred compounds of the present have been found to exhibit advantageous selectivity in that they are potent inhibitors of thrombin, but are much less active and potent in inhibiting plasmin and trypsin.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound the present invention or pharmaceutical composition comprising such a compound.

Definitions

In accordance with the present invention and as used herein, the following terms are defined to have following meanings, unless explicitly stated otherwise.

The term "alkyl" refers to saturated aliphatic groups including straight-chain, branched-chain and cyclic groups.

The term "alkoxy" refers to a group having the formula, R—O—, wherein R is an alkyl group.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkyl" refers to an alkyl group substituted with an aryl group. Suitable aralkyl groups include benzyl, picolyl, and the like, all of which may be optionally substituted.

The term "aralkoxy" refers to a group having the formula, R—O—, wherein R is an aralkyl group.

The term "amino acid" refers to both natural, unnatural amino acids, and their analogs in their D and L stereoisomers, if their structure allows such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(=O)—R—NH—, wherein R typically is —CH(R')—, wherein R' is H or a carbon containing substituent; or (2)

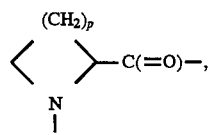

wherein p is 1, 2 or 3 representing the azetidinecarboxylic acid, proline or pipecolic acid residues, respectively.

The term "Ala(3-guanPip)-al" refers to the residue of 3-[3-piperidyl-(N-guanidino)]-alaninal the residue which has the formula:

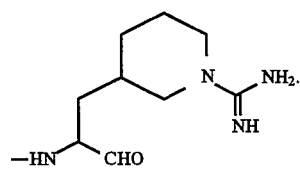

The term "Ala(3-guanPip)-ol" refers to the residue of 3-[3-piperidyl-(N-guanidino)]-alaninol the residue which has the formula:

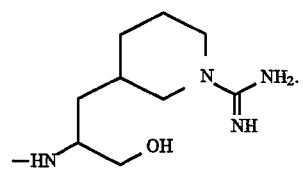

The term "Asp (OCH₃)" refers to L-aspartic acid-(beta methyl ester).

In addition, the following abbreviations stand for the following:

"Boc" refers to t-butoxycarbonyl.

"BOP" refers to benzotriazol-1-yl-oxy-tris-(dimethylamino)-phosphonium hexafluorophosphate.

"Brine" refers to an aqueous saturated solution of sodium chloride.

"BzlSO₂" refers to benzylsulfonyl.

"CBz" refers to benzyloxycarbonyl.

"EDC" refers to 1-ethyl-3-(3-dimethylamino-propyl) carbodiimide hydrochloride salt.

"HBTU" refers to 2-(1H-benzotriazol-1-yl)-1,1,3,3-tetramethyluronium hexafluorophosphate.

"HCl" refers to hydrochloric acid.

"HOBt" refers to 1-hydroxybenzotriazole monohydrate.

"2-PrPen" refers to 2-propylpentanoyl.

"LiAlH₄" refers to lithium aluminum hydride.

"TBTU" refers to 2-(1H-benzotriazol-1-yl)-1,1,3,3-tetramethyluronium tetrafluoroborate.

DETAILED DESCRIPTION OF THE INVENTION

1. Preferred Novel Arginine Mimic Compounds

Figure 1:
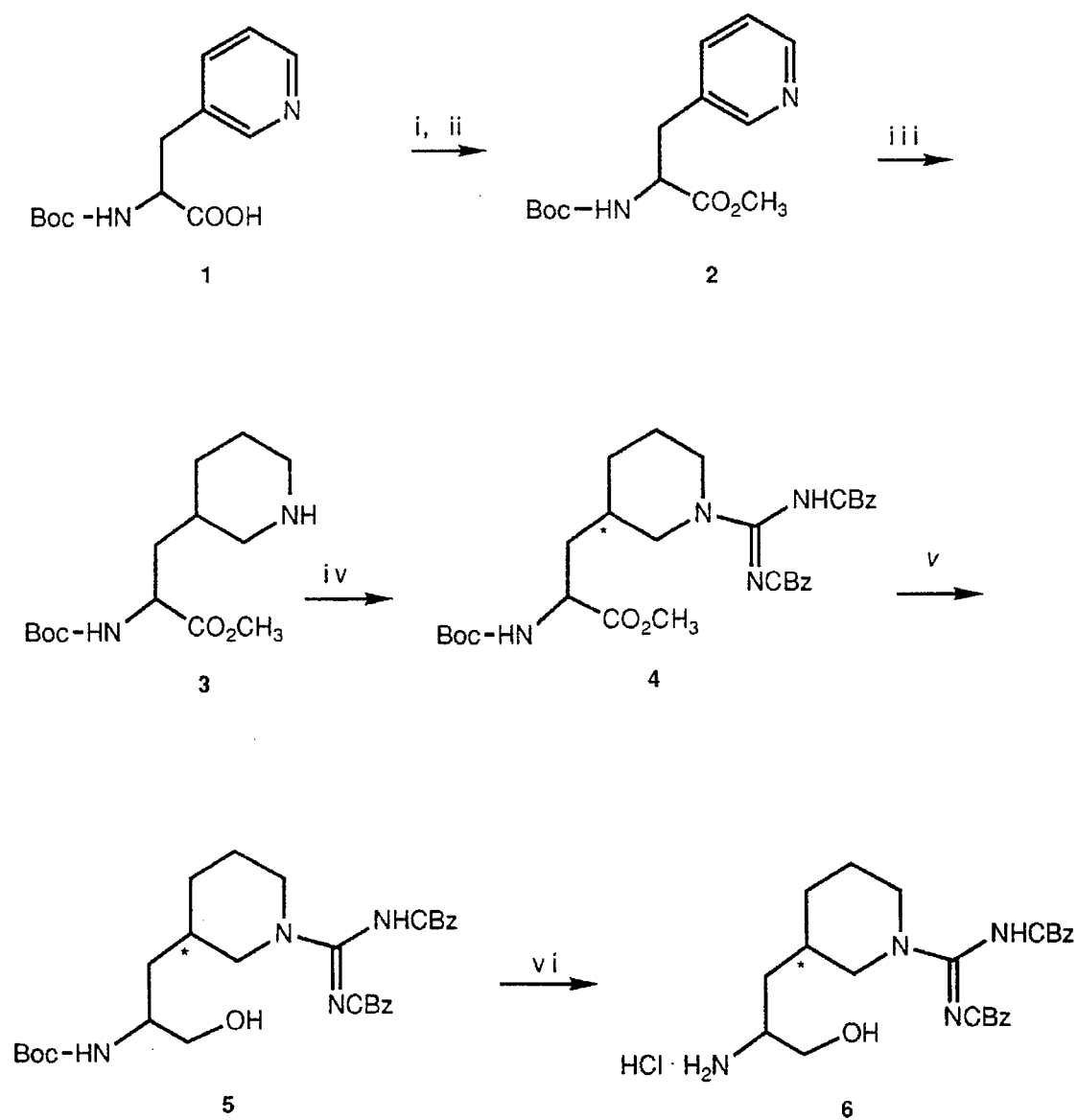
FIG. 1 depicts the reaction scheme for preparation of an intermediate used for the synthesis of the compounds of the present invention. In this figure, "i" through "vi" represent the following: i) thionyl chloride, methanol; ii) di-tert-butyl dicarbonate, pH 7-8; iii) hydrogen gas. platinum oxide in ethanol, water and acetic acid; iv) S-methylisothiourea bis-benzyloxycarbonyl, base, tetrahydrofuran; v) calcium chloride, sodium borohydride in tetrahydrofuran and ethanol; vi) HCl (anhydrous). "*" indicates the position of an asymmetric carbon atom.

Novel compounds of the present invention include compounds of the formula

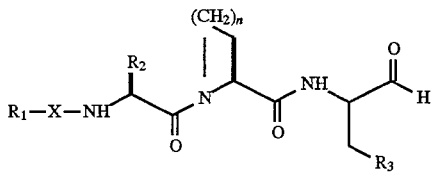

wherein (a) X is selected from the group consisting of —OC(=O)—, —NH—C(=O)—, —C(=O)—, —S(O)$_2$—, —NH—S(O)$_2$— and —N(R')—S(O)$_2$— wherein R' is alkyl of 1 to about 4 carbon atoms, aryl of about 6 to about 14 carbon atoms, or aralkyl of about 6 to about 15 carbon atoms;

(b) R$_1$ is selected from the group consisting of:
  (1) alkyl of about 3 to about 10 carbon atoms,
  (2) alkyl of 1 to about 3 carbon atoms substituted with cyclic alkyl of about 5 to about 8 carbon atoms,
  (3) alkenyl of about 3 to about 6 carbon atoms which is optionally substituted with cyclic alkyl of about 5 to about 8 carbon atoms,
  (4) aryl of about 6 to about 14 carbon atoms which is optionally mono-substituted with Y$_1$ or optionally di-substituted with Y$_1$ and Y$_2$,
  (5) aralkyl of about 6 to about 15 carbon atoms which is optionally mono-substituted in the aryl ring with Y$_1$ or optionally di-substituted in the aryl ring with Y$_1$ and Y$_2$,
  (6) aralkenyl of about 8 to about 15 carbon atoms which is optionally mono-substituted in the aryl ring with Y$_1$ or optionally di-substituted in the aryl ring with Y$_1$ and Y$_2$,

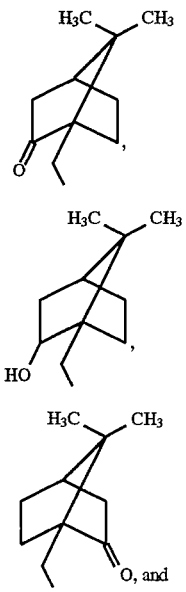

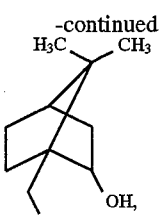

wherein Y$_1$ and Y$_2$ are independently selected from the group consisting of —Z$_1$, —OZ$_1$, —OH, —S(O)$_m$Z$_1$, —S(O)$_3$H, —C(O)OH, —C(O)OZ$_1$, —P(O)$_3$H, and tetrazolyl where m is 0, 1 or 2 and Z$_1$ is alkyl of 1 to about 12 carbon atoms, aryl of about 6 to about 14 carbon atoms and an aralkyl of about 6 to about 15 carbon atoms;

(c) R$_2$ is selected from the group consisting

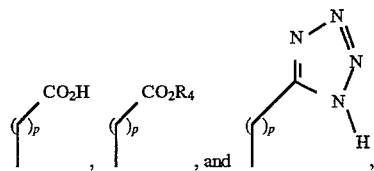

wherein p is 1 or 2 and R$_4$ is selected from the group consisting of alkyl of 1 to about 4 carbon groups, aryl of about 6 to about 15 carbon atoms;

(d) n is 1, 2 or 3;

(e) R$_3$ is selected from the group consisting

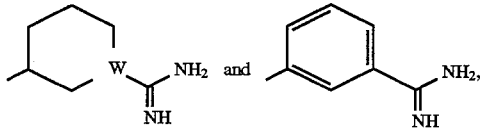

where W is nitrogen or carbon; and pharmaceutically acceptable salts thereof.

Preferred X groups include —C(=O)— and —S(O)$_2$—. Especially preferred are compounds where X is —S(O)$_2$—.

Preferred R$_1$ groups include aralkyl groups and alkyl groups. Preferred alkyl groups include branched chain alkyl groups of 4 to 10 carbon atoms. Such groups include 4-heptyl, 3-methylbutyl and 2,2-dimethylpropyl. Suitable aralkyl groups include unsubstituted and substituted benzyl groups. Preferred substituents on the aryl ring include —C(O)OH, —C(O)OZ$_1$, —S(O)$_m$Z, and —S(O)$_3$H.

Preferred R$_2$ groups include those where p is 1. Also preferred are those R$_2$ groups having either a carboxy or tetrazolyl group. According to an alternate aspect, preferred are those compounds wherein R$_2$ is an ester group.

Preferred are compounds of formula (I) wherein n is 1 or 2; especially preferred are those compounds wherein n is 2.

Preferred R$_3$ groups included those having a saturated six membered ring. Especially preferred are those groups where W is nitrogen.

According to a preferred aspect novel compounds are provided wherein X is —C(=O)— or —S(O)$_2$—, R$_1$ is a branched chain alkyl of at least 4 carbon to 10 carbon atoms, p is 1, n is 2, and R$_3$ is a saturated 6-membered ring wherein W is nitrogen.

According to another aspect, the present invention is directed to salts of the compounds of formula (I). These salts include, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, hydrobromic acid, trifluoroacetic acid, acetic acid, benzene sulfonic acid and other suitable acid addition salts.

2. Preparation of Preferred Compounds a. Preparation of Intermediates.

In an alternative aspect of the present invention, certain intermediates which may be used for the preparation of the compounds of formula (I). For example, 3-[3-piperidyl-(N-guanidino(bis-benzyloxycarbonyl))]-L-alaninol, hydrochloride salt of Example 8 and N-ω-4-methoxy-2,3,6-trimethylbenzene sulfonyl-D,L-3-amidinophenyl alaninal-semicarbazonyl-4-N-diphenylmethane, trifluoroacetate salt of Example 27 are made and coupled to provide certain compounds of the present invention.

FIG. 1 exemplifies a preferred reaction scheme for preparation of one preferred intermediate, 6, which may be used in the preparation of the compounds of the present invention. As shown in FIG. 1, 6 is prepared in stepwise fashion beginning with N-(t-butoxycarbonyl)-3-(3)-pyridyl)alanine, 1 as described below.

1 is esterified with loss of the Boc group, which is then reintroduced to yield an ester, 2. Preferred methods of esterification employ reaction conditions which allow esterification by use of reagents, such as thionyl chloride with an alcohol, anhydrous HCl with an alcohol, or diazomethane in an ether. Especially preferred methods of esterification include the use of thionyl chloride and alcohols. Preferred alcohols include methanol, ethanol, propanol, isopropanol and butanol. Especially preferred alcohols include methyl alcohol. Preferred reagents for re-introducing of the Boc group on to the N-alpha nitrogen of 1 include di-t-butyldicarbonate.

2 is hydrogenated to convert its aromatic ring to a saturated ring to give 3. Preferred methods of hydrogenation include those using hydrogen gas and a catalyst. Preferred catalysts include platinum oxide, rhodium on aluminum and rhodium on carbon. Especially preferred catalysts include platinum oxide.

3 is treated so as to introduce a protected guanidino group to give 4. Preferred methods of introducing a protected guanidino groups would include the reaction of amino group of 3 with bis-protected S-methylisothiourea.

4 is reduced to convert its ester group to an alcohol group to give to 5. Preferred methods of reducing ester groups to alcohol groups include the use of reducing agents such as calcium borohydride, lithium borohydride, sodium borohydride, lithium aluminum hydride or sodium metal in ethanol. Especially preferred methods of reduction include the use of calcium borohydride.

5 is treated to convert its Boc-protected amino group to a free N-alpha amino group to give 6. Preferred methods of removing the Boc group include treatment of 5 with HCl in alcohol, trifluoroacetic acid in a chlorinated hydrocarbon solvent, HCl in acetic acid, HCl in ethereal solvents, HCl in ethyl acetate or methyl acetate, p-toluenesulfonic acid in toluene. Especially preferred methods include treatment of 5 with anhydrous HCl in ethyl acetate at 15°–30° C., more preferably at 20°–25° C.

b. Coupling.

The compounds of the present invention are conveniently prepared by chemically coupling an intermediate of the present invention, as for example, 3-[3-piperidyl-(N-guanidino(bis-benzyloxycarbonyl))]-L-alaninol, hydrochloride salt of Example 8, or N-ω-4-methoxy-2,3,6-trimethylbenzene sulfonyl-D,L-3-amidinophenyl alaninal-semicarbazonyl-4-N-diphenylmethane, trifluoroacetate salt of Example 27, to Pr-HN-AA$_1$-AA$_2$...AA$_k$-OH.

Pr-HN-AA$_1$-AA$_2$...AA$_k$-OH refers to a protected amino acid, protected amino acid analog, or protected peptide, having a free C-terminal carboxy group. "k" is an integer, preferably ranging from 1 to 30, which gives the number of amino acids, amino acid analogs, or combination of amino acids and amino acid analogs which comprise Pr-HN-AA$_1$-AA$_2$...AA$_k$-OH. Where "k" is 1, Pr-HN-AA$_1$-OH is a protected amino acid or protected amino acid analog. Where is 2 to 30, Pr-HN-AA$_1$-AA$_2$...AA$_k$-OH is a protected peptide comprised of "k" amino acids, amino acid analogs or some combination of amino acids and amino acid analogs, the total number of which equals "k". Especially preferred for Pr-HN-AA$_1$-AA$_2$...AA$_k$-OH is wherein "k" is 1 to 10. More especially preferred for Pr-HN-AA$_1$-AA$_2$...AA$_k$-OH include those wherein "k" is 2 to 5. "Pr" refers to a protecting group for the N-terminal amino acid or amino acid analog of Pr-HN-AA$_1$-AA$_2$...AA$_k$-OH.

The term "protected" refers to the presence of protecting groups on the N-terminal amino group, and if necessary, on the side chain functional groups of the constituent amino acids, amino acid analogs or combination of amino acids and amino acid analogs comprising Pr-HN-AA$_1$-AA$_2$...AA$_k$-OH.

Suitable N-terminal amino protecting groups which can be removed under non-adverse conditions include:

(a) aromatic urethane-type protecting groups which include benzyloxycarbonyl, 2-chlorobenzyloxycarbonyl, 9-fluorenylmethyloxycarbonyl, isonicotinyloxycarbonyl and 4-methoxybenzyloxycarbonyl;

(b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl;

(c) cycloalkyl urethane-type protecting groups which include adamantyloxycarbonyl, cyclopentyloxycarbonyl, cyclohexyloxycarbonyl and isobornyloxycarbonyl. Preferred N-terminal protecting groups include benzyloxycarbonyl and t-butoxycarbonyl. Especially preferred protecting groups include t-butoxycarbonyl. The term "non-adverse conditions" refers to conditions for removing protecting groups which do not adversely affect the skeleton of the peptide and/or its amino acid (and/or amino acid analog) constituents.

Suitable N-terminal amino protecting groups which cannot be removed under non-adverse conditions may also be used. These include acyl protecting groups or sulfonyl protecting groups. Preferred non-removable protecting groups include acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl.

Suitable side-chain protecting groups which can be removed under non-adverse conditions include:

(a) for the guanidino group of arginine, protecting groups include nitro, benzyloxycarbonyl, t-butoxycarbonyl, 2,2,5,7,8-pentamethylchroman-6-sulfonyl, 2,3,6-trimethyl-4-methoxyphenylsulfonyl and 4-methylbenzenesulfonyl;

(b) for the carboxyl group of aspartic acid or glutamic acid, protecting groups include the methyl ester, ethyl ester, t-butyl ester and benzyl ester; and Protecting groups for the N-terminal amino group and side chain groups of amino acids and peptides such as those disclosed above are well known in the art. See Bodanszky, N., Peptide Chemistry, pp. 74–103, Springer-Verlag, N.Y. (1988) and references cited therein.

Pr-HN-AA$_1$-AA$_2$ . . . AA$_k$-OH may be made by solid-phase or solution phase methods. Preferred synthesis methods for the straight-chain peptides, especially the smaller peptides (of shorter chain length, that is, having from about 3 to about 50 amino acid residues), such as Pr-HN-AA$_1$-AA$_2$ . . . AA$_k$-OH, include the solid-phase method. This method is well known in the art and has been described in Merrifield, J. Am. Chem. Soc., 85: 2149–2154 (1963); Science, 150: 178–185 (1965); and Science, 232: 341–347 (1986); Vale et al., Science 213: 1394–1397 (1981); and Marke et al. J. Am. Chem. Soc., 103: 3178 (1981); the disclosures of which are incorporated herein by reference. Other preparative methods which may be employed include the processes of Houghten, et. al., Proc. Natl. Acad. Sci (USA), 82: 5132 (1985).

Solid-phase peptide synthesis is generally commenced from the C-terminus of the peptide by coupling the first N-alpha-protected amino acid to a suitable resin, such as a hydroxymethylphenoxymethyl polystyrene resin (HMP) or a RINK ([dimethoxyphenyl-Fmoc aminomethyl]-phenoxy) resin when synthesizing a peptide amide. The RINK resin is a modified benzhydrylamine resin that contains ortho and para electron-donating methoxy groups.

During synthesis, suitable protecting groups as described above are used to prevent side reactions with functional groups on amino acid side-chains as needed. The peptide sequence is synthesized by sequential coupling of these protected amino acids to the amino-terminal end of the growing peptide chain attached to the solid support. After the desired peptide sequence is complete, the intermediate peptide is cleaved from the resin. The peptide is isolated by techniques such as filtration, centrifugation or extraction with diethyl ether. The peptide can then be purified by high performance liquid chromatography (HPLC) or other such methods of protein purification. Suitable recovery methods for synthesized peptides are described in the foregoing references. Other recovery methods which may be employed include those described in Rivier et al., Peptides: The Structure and Biological Function, pages 125–128 (1979), the disclosures of which are incorporated herein by reference.

The intermediates of the present invention are chemically coupled to Pr-HN-AA$_1$-AA$_2$ . . . AA$_k$-OH using conventional coupling reagents known in the art. See Bodanszky, N., Peptide Chemistry, pp. 55–73, Springer-Verlag, N.Y. (1988) and references cited therein. The chemical coupling may be performed by either one-step or two-step coupling methods. In the one-step coupling methods, Pr-HN-AA$_1$-AA$_2$ . . . AA$_k$-OH is coupled directly to an intermediate of the present invention. Preferred coupling reagents for one-step coupling include DCC with HOBt, EDC with HOBt, HBTU, TBTU, HBTU with HOBt or TBTU with HOBt. In the two-step coupling methods, an activated ester or anhydride of the C-terminal carboxy group of Pr-HN-AA$_1$-AA$_2$ . . . AA$_k$-OH is formed prior to or during the chemical coupling with an intermediate of the present invention. Preferred reagents for use in two-step coupling methods include DCC with HOBt or EDC with HOBt.

Figure 2:
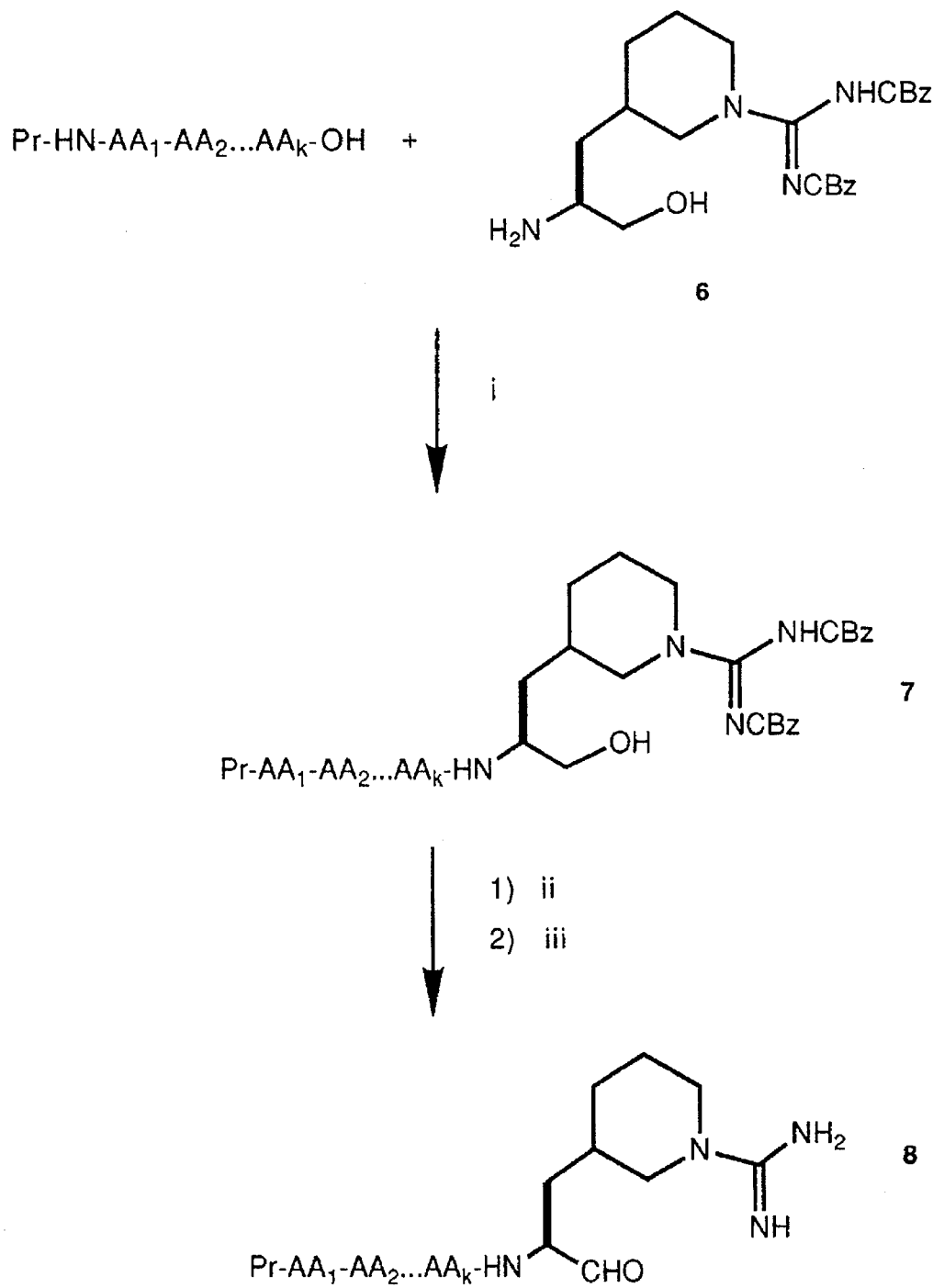
FIG. 2 depicts the reaction scheme for preparation of the compounds of the present invention using an intermediate (compound 6 of FIG. 1). In this figure, "Pr" refers to a protecting group on the N-alpha amino group of the N-terminal amino acid or amino acid analog, "AA₁-AA₂. . . AA_k" refers to a peptide wherein "AA" refers to an amino acid or amino acid analog and "k" is an integer. Also, in this figure, "i" through "iii" are defined as: i) HOBt, EDC; ii) hydrogen gas. 10% palladium on carbon; and iii) dimethyl sulfoxide, toluene, dichloroacetic acid, EDC.

FIG. 2 discloses a preferred reaction scheme for preparation of certain compounds of the present invention which includes the coupling of the intermediate, 3-[3-piperidyl-(N-guanidino(bis-benzyloxycarbonyl))]-L-alaninol, 6 to Pr-HN-AA$_1$-AA$_2$ . . . AA$_k$-OH to give 7. Examples 9, 17, 28 and 33 disclose the coupling of certain intermediates of the present invention to a protected dipeptide representing Pr-HN-AA$_1$-AA$_2$ . . . AA$_k$-OH, where k is 2.

c. Deprotection.

Upon completion of the coupling step, the protecting groups on the intermediate coupled to Pr-HN-AA$_1$-AA$_2$ . . . AA$_k$-OH are chemically removed. The preferred method for chemically removing such protecting groups depends on their identity.

Where the protecting groups are benzyloxycarbonyl groups, the preferred methods of removal include hydrogenation using hydrogen gas and a catalyst. Preferred catalysts include palladium on carbon. For example, as shown in FIG. 2, the benzyloxycarbonyl groups of intermediate coupled to form 7 are removed by hydrogenation. Examples 10, 18 and 34 disclose the use of a hydrogenation step to remove such protecting groups. Examples 29 and 30 disclose the removal in two steps of a N-$\omega$-4-methoxy-2,3,6-trimethylbenzenesulfonyl protecting group and semicarbazonyl-4-N-diphenylmethyl protecting group from the intermediate coupled to a dipeptide. The disclosed removal steps includes treatment with hydrofluoric acid and treatment with formalin.

d. Further chemical conversions.

Upon completion of the deprotection step, and if necessary, the deprotected coupled product, is chemically converted to a compound of the present invention. For example, as shown in FIG. 2, alcohol functional group on 7 (after deprotection) is converted to an aldehyde functional group by oxidation to give a compound of the present invention 8. The preferred methods of oxidation include methods using dimethyl sulfoxide, toluene, dichloroacetic acid and EDC; or methods using pyridine sulfur trioxide, triethylamine and dimethylsulfoxide. Especially preferred methods of oxidation include the method using dimethyl sulfoxide, toluene, dichloroacetic acid and EDC.

Further, if there are protecting groups on the N-terminal amino group of Pr-HN-AA$_1$-AA$_2$ . . . AA$_k$-OH of the coupled product and/or on side chain groups of the amino acid or amino acid analogs of Pr-HN-AA$_1$-AA$_2$ . . . AA$_k$-OH, they are chemically removed. For example, if such protecting groups are t-butoxycarbonyl, t-amyloxycarbonyl, isobornyloxycarbonyl, adamantyloxycarbonyl, 4-methoxybenzyloxycarbonyl or 2-(4-biphenyl)-2-propyloxycarbonyl, preferred methods of chemically removing them include their treatment with a liquid mixture comprised of an acid and solvent. Preferred methods include chemically removal by treatment with HCl in alcohol, trifluoroacetic acid in a chlorinated hydrocarbon solvent, HCl in acetic acid, HCl in ethereal solvents, HCl in ethyl acetate or methyl acetate, p-toluenesulfonic acid in toluene. Especially preferred methods of removal include treatment with trifluoroacetic acid in dichloromethane at 0°–30° C., more preferably at 20°–25° C. Alternatively, where such protecting groups include benzyloxycarbonyl, isonicotinyloxycarbonyl or 2-chlorobenzyloxycarbonyl, the preferred methods of chemically removing them include their treatment with hydrogen gas or a source of hydrogen gas in a liquid mixture comprised of catalyst and solvent, as for example, hydrogen gas on platinum or palladium in a liquid mixture comprised of alcohol, with 1,4-cyclohexadiene and platinum or palladium in a liquid mixture comprised of alcohol, or with ammonium formate and platinum or palladium in a liquid mixture comprised of 50% aqueous acetic acid. Especially preferred methods of chemical removal include treatment with hydrogen gas on palladium in a liquid mixture comprised of alcohol and acid, as for example, ethanol and acetic acid.

3. Selection of Preferred Compound.

The compounds of the present invention are screened for their ability to inhibit thrombin, plasmin, tissue plasminogen activator (t-PA), activated protein C (aPC), chymotrypsin, and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and trypsin for a given compound is greater than or equal to its $IC_{50}$ (or $K_i$, respectively) for thrombin.

The compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. $K_i$ is that concentration of test compound giving 50% inhibition of the rate of substrate turnover. Examples A, B and C provide an exemplars of the in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a Ki of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the reported $IC_{50}$ is considered to be that highest concentration of compound tested.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remington's Pharmeceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutcial compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of BOc-L-aspartyl-(beta-methyl ester)-L-proline-O-benzyl ester

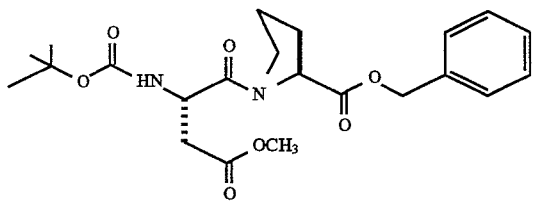

To a solution of isobutylchloroformate (40.2 mL, 0.310 mole) and 1000 mL of ethyl acetate at 0° C. was added slowly N-methylmorpholine (51.2 mL, 0.465 mole). The mixture was stirred for 10 minutes with a mechanical stirrer. Boc-L-aspartic acid (beta-methyl ester) (75 g, 0.283 mole) was added as a solid. The resulting solution was stirred for 15 minutes. Next, solid L-proline-O-benzyl ester hydrochloride salt (75 g, 0.310 mole) was added followed by the slow addition of N-methylmorpholine (44.4 mL, 0.403 mole). After 30 minutes, the ice bath was removed and the reaction was monitored by thin layer chromatography (silica gel, 5:95 methanol/dichloromethane). The reaction was completed after about 2 hours and the resulting organic phase was poured into 1 liter of water. The organic phase was separated and washed three times with 300 mL of 1N HCl, one time with 300 mL saturated sodium bicarbonate and one time with 100 mL of brine. The organic phase was dried over anhydrous magnesium sulfate, filtered and the solvent was removed under vacuum to give 120.2 g (91%) of the title compound as a yellow oil. Thin-layer chromatography gave a Rf=0.76 (silica gel; 5:95 methanol/dichloromethane).

Example 2

N-(2-propylpentanoyl)-L-aspartyl-(beta-methyl ester)-L-proline-O-benzyl ester

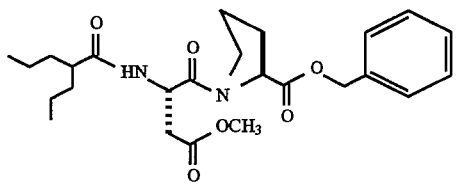

To a solution of the compound of Example 1 (112.6 g, 0.259 mole) and 400 mL of ethyl acetate at 0° C., 700 mL of ethyl acetate saturated with HCl (g) was added with stirring. After about 1 hour, the reaction was complete as indicated by thin-layer chromatography (silica gel, 5:95 methanol/dichloromethane). After removing the solvent under vacuum, the resulting solid was suspended in 500 mL of ethyl acetate to give a solution of L-aspartyl-(beta-methyl ester)-L-proline-O-benzyl ester hydrochloride salt.

To a solution of isobutylchloroformate (28.6 mL, 0.220) and 300 mL of ethyl acetate at 0° C. was added slowly N-methylmorpholine (31.3 mL, 0.285 mole). The mixture was stirred at 0° C. for 10 minutes; then, 2-propylpentanoic acid (34.5 mL, 0.220 mole) was added. The resulting solution was stirred for 30 minutes and then added to the suspension of L-aspartyl-(beta-methyl ester)-L-proline-O-benzyl ester hydrochloride salt prepared above at 0° C. To this suspension was added slowly N-methylmorpholine (31.3 mL, 0.389 mole). The ice bath was removed after 30 minutes and the reaction mixture was allowed to warm to 25° C. After about 3 hours, the reaction was complete as determined by thin-layer chromatography (silica gel, 5:95 methanol/dichloromethane) and the resulting organic phase was poured into 1 liter of water. The organic phase was separated and washed three times with 1N HCl (3×100 mL), three times with saturated sodium bicarbonate (3×100 mL) and one time with brine (100 mL). The organic phase was dried over anhydrous magnesium sulfate, and filtered; the solvent was removed under vacuum to give a residue.

The residue was chromatographed on silica gel (230–400 mesh, 14×70 cm column) and eluted with a gradient of 0 to 3% methanol in dichloromethane. The solvents were evaporated to yield of the 106.8 g (90%) of the title compound as a yellow oil. Thin-layer chromatography gave a Rf=0.73 (silica gel; 5:95 methanol/dichloromethane).

Example 3

N-(2-propylpentanoyl)-L-aspartyl-(beta-methyl ester)-L-proline

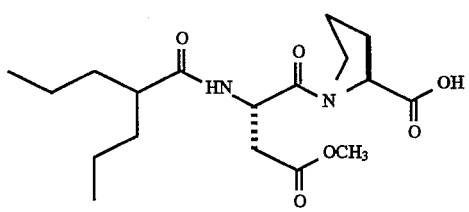

To a mixture of the compound of Example 2 (111.6 g, 0.242 mole), 500 mL of methanol and 11 g of 10% palladium on carbon (wet with dichloromethane), hydrogen gas was added via a balloon. The reaction mixture was stirred overnight at 25° C. The following day, the reaction was complete as determined by thin-layer chromatography (silica gel, 5:95 methanol/dichloromethane). The solution was filtered through celite and and the celite was washed with dichloromethane (200 mL). The organic solvent was evaporated under vacuum. The resulting white solid was triturated with 300 mL of diethyl ether, filtered and dried to yield 47.3 g (58%) the title compound. Thin-layer chromatography gave a Rf=0.23 (silica gel; 20:80 methanol/dichloromethane).

Example 4

Preparation of N-(t-butoxycarbonyl)-3-(3-pyridyl)-L-alanine methyl ester

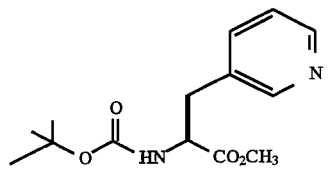

To a solution of N-(t-butoxycarbonyl)-3-(3-pyridyl) alanine (5.0 g, 18.8 mmole) in methanol (100 mL) was added thionyl chloride (2M solution in dichloromethane, 66 mL, 132 mmole). The resulting solution was stirred overnight at ambient temperature. The methanol was removed under reduced pressure to a minimum volume and ethyl acetate (100 mL) was added. The resulting white precipitate was collected in a fritted funnel. To a solution of the collected precipitate in a mixture of tetrahydrofuran/water (40 mL each) was added di-tert-butyl dicarbonate (4.8 g, 21.99 mmole ) and sodium carbonate (1.95 g, 18.4 mmole). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This product was subjected to flash column chromatography on silica gel (230–400 mesh) using a 8×52 cm column and eluting with a 10:90 mixture of ethyl acetate/hexane followed by a 60:40 mixture of ethyl acetate/hexane. 4 g (74%) of the title compound was obtained as an oil. Thin-layer chromatography gave a Rf=0.68 (silica gel; ethyl acetate).

Example 5

Preparation of N-(t-butoxycarbonyl)-3-(3-piperidyl)-L-alanine methyl ester, acetate salt

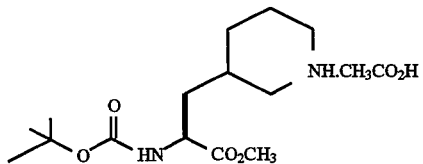

A solution of the compound of Example 4 (5 g, 17.8 mmole) in ethanol (24 mL), acetic acid (6 mL) and water (6 mL) was hydrogenated over platinum oxide (500 mg) at 45 psi for three hours. The catalyst was filtered off and the filtrate concentrated under vacuum to an oily residue (6.89 g) which was used in the next step (Example 6) without further purification. Thin-layer chromatography yielded two spots corresponding to two diastereomers with $R_f$ values of 0.16 and 0.26, respectively (silica gel; 4:1:1 n-butanol/acetic acid/water).

Example 6

Preparation of N-(t-butoxycarbonyl)-3-[3-piperidyl-(N-guanidino (bis-benzyloxycarbonyl))]-L-alanine methyl ester

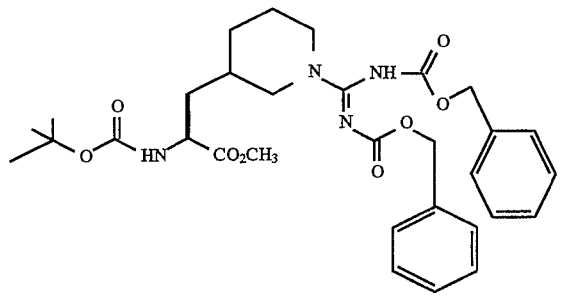

To a solution of the compound of Example 5 (6.89 g, 19.9 mmole) in tetrahydrofuran (80 mL) was added S-methylisothiourea bis-benzyloxycarbonyl (7.13 g, 19.9 mmole) followed by N-methylmorpholine (4.37 mL), and the reaction mixture was stirred at ambient temperature for 18 hours. The reaction mixture then was concentrated under vacuum and the resulting residue was dissolved in ethyl acetate (100 mL) and washed with 1N sodium bisulfate and saturated sodium chloride (50 mL each). After drying over anhydrous sodium sulfate, the solvents were removed under vacuum; the crude title compound was subjected to flash column chromatography on silica gel (230–400 mesh) using a 8×52 cm column and eluting with 1:9 ethyl acetate/hexanes (two column volumes) followed by 1:1 ethyl acetate/hexanes. 2.75 g the title compound was obtained as a mixture of two diastereomers. Thin-layer chromatography gave two spots with Rf values of 0.57 and 0.62, respectively (silica gel; 1:1 ethyl acetate/hexanes).

Example 7

Preparation of N-(t-butoxycarbonyl)-3-[3-piperidyl-(N-guanidino (bis-benzyloxycarbonyl))]-L-alaninol

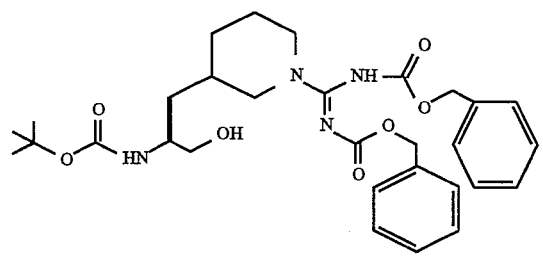

To a stirred solution of the compound of Example 6 (2.23 g, 3.7 mmole) in absolute ethanol (8 mL) and anhydrous tetrahydrofuran (4 mL) was added calcium chloride (844 mg, 7.6 mmole) and sodium borohydride (575 mg, 15.2 mmole). After stirring 12 hours at ambient temperature, the reaction mixture was concentrated under vacuum and the resulting residue was partitioned between ethyl acetate and 1N sodium bisulfate (10 mL each). The two layers were separated; organic layer was washed twice more with 1N sodium bisulfate, dried over anhydrous sodium sulfate and concentrated under vacuum gave a residue. Flash column chromatography of the residue on silica gel (230–400 mesh) using a 5.5×45 cm column and eluting with ethyl acetate gave 1.3 g of the title compound as a white foam. Thin layer chromatography yielded two spots corresponding to two diastereomers with $R_f$ values of 0.18 and 0.27, respectively (silica gel; 1:1 ethyl acetate/hexanes).

Example 8

Preparation of 3-[3-piperidyl-(N-guanidino (bis-benzyloxycarbonyl))]-L-alaninol, hydrochloride salt

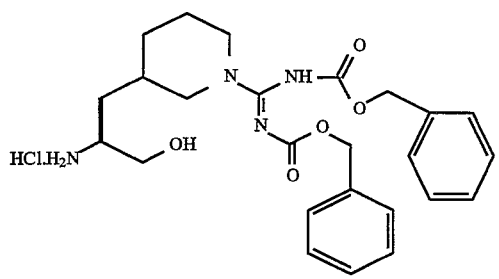

The compound of Example 7 (290 mg, 0.57 mmole) was treated with 2.5N anhydrous hydrochloric acid in ethyl acetate (2.0 mL) at ambient temperature for one hour. The solvent was removed under vacuum to a sticky-white solid (260 mg). This solid was used in the next step (Example 9) without further purification. $^1$H NMR spectrum taken in $CD_3OD$ showed no t-butoxycarbonyl protons at 1.4 ppm.

Example 9

Preparation of alpha-N-(2-propylpentanoyl)-aspartyl (beta-methyl ester)-prolyl-3-[3-piperidyl-(N-guanidino (bis-benzyloxycarbonyl))]-L-alaninol

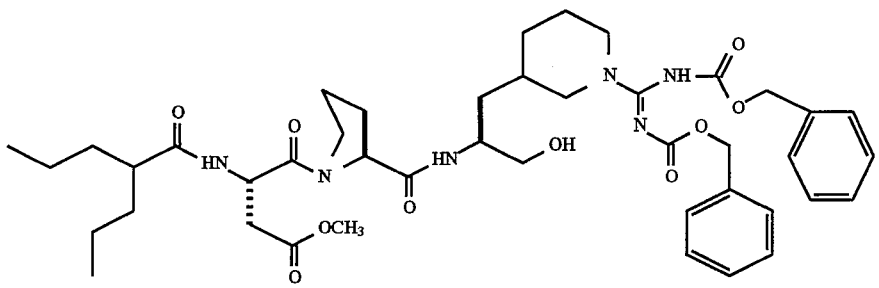

To a suspension of the compound of Example 8 (2.06 g, 4.08 mmole) in acetonitrile (22 mL) was added successively the compound of Example 3 (2.06 g, 5.56 mmole), EDC (1.12 g, 5.84 mmole), 1-hydroxybenzotriazole hydrate (979 mg, 6.39 mmole), and N-methylmorpholine (3 mL, 27.80 mmole). The solution was stirred at ambient temperature for twelve hours. The solvent was removed under vacuum and the resulting residue was dissolved in a 9:1 mixture of dichloromethane/isopropanol (40 mL) and washed two times each with 15 mL portions of 1N sodium bisulfate, saturated sodium bicarbonate and saturated sodium chloride. The organic layer was dried over anhydrous sodium sulfate and concentrated under vacuum. The crude title compound was chromatographed on a 5.5×45 cm silica gel (230–400 mesh) column eluting with ethyl acetate (two column volumes), followed by 9:1 dichloromethane/isopropanol (two column volumes). 1.85 g of the title compound was obtained which consisted of a mixture of two diastereomers. Thin-layer chromatography showed two spots with $R_f$ values of 0.4 and 0.32, respectively (silica gel; 9:1 dichloromethane/methanol).

Example 10

Preparation of alpha-N-(propylpentanoyl)-aspartyl (beta-methyl ester)-prolyl-3-[3-piperidyl-(N-guanidino)]-L-alaninol

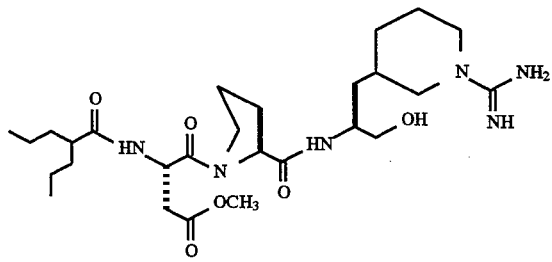

The compound of Example 9 (1.85 g, 2.25 mmole) was subjected to catalytic hydrogenation in methanol (100 mL) and acetic acid (10 mL) in the presence of 10% palladium on carbon (185 mg) at 30 psi for 2.5 hours. The catalyst was filtered off and the filtrate was concentrated to an oily residue (1.46 g). The fast and slow diastereomers were analyzed by analytical HPLC using a reverse phase column containing a C-18 resin comprised of a 10 micron-size gel particles with a 300 angstrom pore size and were found to have retention times of 17.5 and 20 min, respectively.

Example 11

Preparation of alpha-N-(propylpentanoyl)-aspartyl (beta-methyl ester)-prolyl-3-[3-piperidyl-(N-guanidino)]-L-alaninal

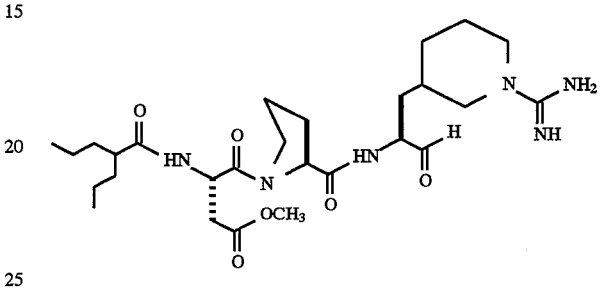

To a chilled solution of the compound of Example 10 (0.76 g, 1.4 mmole) in dimethylsulfoxide and toluene (15 mL each) was added dichloroacetic acid (567 mL, 6.9 mmole), followed by EDC (2.68 g, 14 mmole) at one minute later. The reaction mixture was stirred for 5 minutes at 0° C., 85 minutes at ambient temperature, and then was quenched with 60 mL water. The water layer was extracted twice with diethyl ether (10 mL portions) and the remaining water layer was subjected to HPLC using a 47×300 mm reverse phase column containing a C-18 resin comprised of a 10 micron-size gel particles with a 300 angstrom pore size. The column was eluted with a gradient ranging from 15% to 30% acetonitrile in water (containing 0.1% trifluoroacetic acid). The oxidation was repeated with 0.7 g additional material and purified in a similar manner. The HPLC fractions containing the title compound from both reactions were pooled then lyophilized to yield 549 mg of the faster moving diastereomer with a retention time of 17 minutes (referred to isomer "11A") and 204 mg of the slower moving diastereomer with a retention time of 19 minutes (referred to as isomer "11B"). Fast atom bombardment mass spectrometry confirmed the theoretical molecular weight of 550 for both diastereomers.

Example 12

Preparation of alpha-N-Boc-L-alanyl-(beta-cyano)-L-proline-O-methyl ester

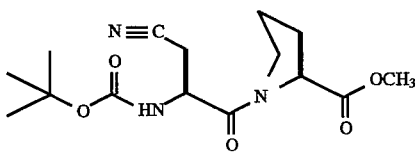

20.1 g (87 mmole, 1 equivalent) of Boc-L-asparagine was dissolved in 173 mL acetonitrile. 25.2 mL (1.7 equivalents) of diisopropylethylamine was added and the mixture was stirred for about 15 minutes until all the solids had dissolved. 25.0 g (1.2 equivalents) of EDC was added and the mixture was stirred for an additional 4 hours at room temperature.

After this time, 16.6 g (1.0 equivalent) of additional EDC and 17.23 g (1.2 equivalents) of L-proline-O-methyl ester hydrochloride was added and the mixture was stirred for about 15 hours. The reaction mixture was reduced in volume under vacuum, then was partitioned between 2 L of ethyl acetate and 200 mL of 0.5M potassium bisulfate. After the layers were separated, the organic layer was washed successively with 0.5M potassium bisulfate (200 mL), saturated sodium bicarbonate (2×200 mL), and brine (200 mL), and then was dried over anhydrous sodium sulfate. The solvent was then removed under vacuum to yield 29 g (60%) of the title compound as white solid. NMR (CDCl$_3$): (ppm) 5.4 (d, 1H); 4.8 (m, 1H); 4.55 (m, 1H); 3.7 (m, 4H)2.75 (m, 2H); 2.35 (m, 1H); 2.05 (m, 2H); 1.65 (m, 2H); 1.40 (s, 9H).

Example 13

Preparation of Boc-L-alanyl-(beta-tetrazol-5-yl)-L-proline-O-methyl ester

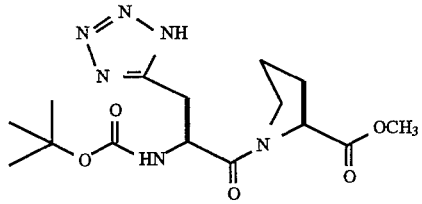

12.72 g (33.6 mmole, 1 equivalent) of the compound of Example 12 and 10.9 g (5 Eq.) of sodium azide NaN$_3$ were combined in 135 mL dimethylformamide. To this solution, 37 g (8.0 Eq.) of ethylamine hydrochloride was added. The reaction mixture was refluxed at 90° C. for 60 hours behind a blast shield. After this time, the reaction mixture was allowed to cool, then was filtered to remove solids. The solids which had collected on the filter were rinsed with dimethylformamide. The combined flitrates were reduced to a residue under vacuum, then were taken up in 500 mL of ethyl acetate. The ethyl acetate solution was washed with saturated sodium bicarbonate (2×200 mL). The combined aqueous layers were acidified to pH 2 with 6M HCl, and then extracted with ethyl acetate (2×200 mL). The combined organic layers were dried over anhydrous sodium sulfate. The solvents were removed under vacuum to give the title compound (10.2 g, 83% yield) as a white foam. NMR (CDCl$_3$): (ppm) 5.55 (d, 1H); 4.82 (m, 1H); 4.55 (m, 1H); 3.8 (s, 3H); 3.7 (m, 1H); 3.55 (m, 1H); 3.32 (m, 2H); 2.3 (m, 1H); 2 (m, 3H); 1.42 (s, 9H).

Example 14

Preparation of L-alanine-(beta-tetrazol-5-yl)-L-proline-O-methyl ester

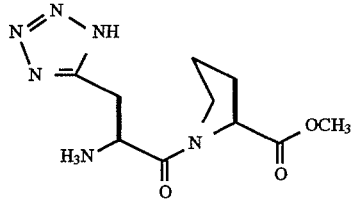

10 g (27.2 mmole, 1 equivalent) of the compound of Example 13 was dissolved in 100 methanol; the resulting solution was saturated with gaseous HCl and allowed to stir at room temperature for 45 minutes. 50 mL of toluene was added and the reaction mixture was reduced in volume under vacuum to give a residue. The residue was redissolved in 100 mL of methanol and 50 mL of toluene, then was again reduced in volume under vacuum to give the title compound (8g, 97% yield) as a yellow foam. NMR(CD$_3$OD): (ppm) 4.75 (m, 1H); 4.5 (m, 1H); 3.75 (m, 1H); 3.7 (s, 3H); 3.65 (m, 1H); 3.45 (m, 2H); 2.3 (m, 1H); 2.05 (m, 3H).

Example 15

Preparation of alpha-N-(2-propylpentanoyl)-L-alanine-(beta-tetrazol-5-yl)-L-proline-O-methyl ester

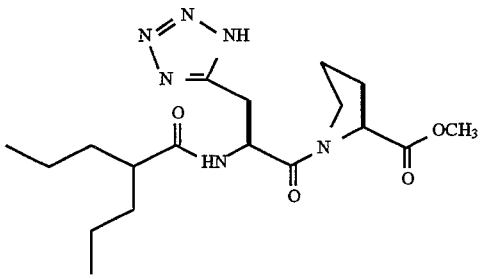

109 mL of tetrahydrofuran was added to 8 g (26.4 mmole, 1 equivalent) of the compound of Example 14, followed by 6.6 g of 2-propylpentanoyl chloride (1.5 equivalents). To this stirred solution, 28 mL (6 equivalents) of diisopropylethylamine was added. The reaction was allowed to stir at room temperature for 20 hours. After this time, the reaction mixture was reduced in volume under vacuum to a residue. The residue was partitioned between 400 mL of ethyl acetate and 100 mL of 0.5M potassium bisulfate. The layers were separated. The organic layer was washed with 100 mL 0.5M potassium bisulfate and 100 mL of brine, dried over anhydrous sodium sulfate, then reduced in volume under vacuum to a residue. The residue was purified by flash chromatography using a 80×240 mm silica gel column, eluting with a gradient ranging from 5–25% methanol in dichloromethane to give 4.92 g (46%) of the title compound. NMR(CDCl$_3$): (ppm) 6.72 (d, 1H); 5.1 (m, 1H); 4.6 (m, 1H); 3.75 (m, 2H); 3.6 (m, 2H); 3.4 (m, 2H); 2.35 (m, 1H); 2.1 (m, 3H); 1.55 (m, 2H); 1.38 (m, 2H); 1.22 (m, 4H); 0.9 (m, 6H).

Example 16

Preparation of alpha-N-(2-propylpentanoyl)-L-alanine-(beta-tetrazol-5-yl)-L-proline

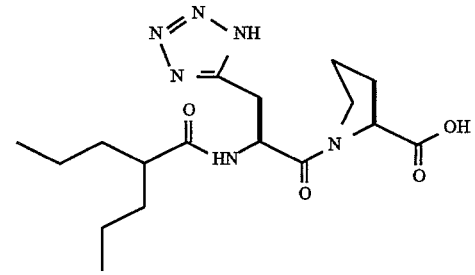

4.92 g (12.5 mmole, 1 equivalent) of the compound of Example 15 was added to 83 mL of methanol, followed by 28 mL (2.2 equivalents) lithium hydroxide (as a 1M solution in water). The reaction mixture was allowed to stir at room temperature for 16 hours. After this time, the mixture was poured over a 50 mL bed of Dowex (50×8–400) and was eluted with 250 mL of 50:50 water/methanol. The eluent was reduced in volume under vacuum to a solid, then was dried overnight under high vacuum to give 4.60 g, (97% yield) of the title compound. NMR(CDCl₃): (ppm) 7.35 (d, 1H); 5.3 (m, 1H); 4.5 (m, 1H); 3.88 (m, 1H); 3.6 (m, 2H); 3.45 (m, 1H); 2.25 (m, 2H); 2.0 (m, 3H); 1.55 (m, 2H); 1.35 (m, 2H); 1.20 (m, 4H); 0.82 (m, 6H).

Example 17

Preparation of alpha-N-(2-propylpentanoyl)-L-alanyl-(beta-tetrazol-5-yl)-L-prolyl-L-3-[3-piperidyl-(N-guanidino(bis-benzyloxycarbonyl))]-L-alaninol

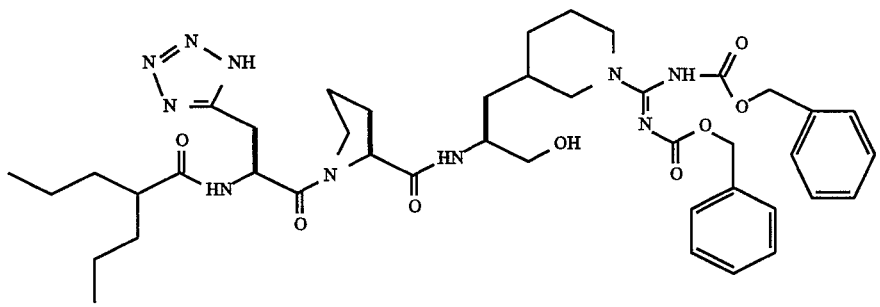

To a suspension of the compound of Example 8 (0.68 g, 1.35 mmole) in acetonitrile (5 mL) was added successively the compound of Example 16 (430 mg, 1.13 mmole), EDC (323 mg, 1.68 mmole), dimethylaminopyridine (14 mg, 0.11 mmole), and diisopropylethylamine (1.17 mL, 4.3 mmole). The solution was stirred at ambient temperature for 12 hours. The solvent was removed under vacuum and the resulting residue was taken up in ethyl acetate and washed two times each with 5 mL portions of 1N sodium bisulfate and saturated sodium chloride. The organic layer was dried over anhydrous sodium sulfate and the solvent was removed under vacuum to give crude product. This product was chromatographed on a 3.5×52 cm column of silica gel (230–400 mesh), eluting with 9:1 dichloromethane/methanol (two column volumes), followed by 85:10:5 dichloromethane/methanol/acetic acid. The solvents were removed from the eluent to give 530 mg (56%) of the title compound as a mixture of two diastereomers. Analytical HPLC using a 4.6×250 mm reverse phase column containing a C-18 resin comprised of a 10 micron-size gel particles with a 300 angstrom pore size and eluting with a gradient ranging from 5–75% acetonitrile in water (containing 0.1% trifluoroacetic acid) yielded one peak with a retention time of 14.5 minutes.

Example 18

Preparation of alpha-N-(2-propylpentanoyl-L-alanyl-(beta-tetrazol-5-yl)-prolyl-3-[3-piperidyl-(N-guanidino)]-L-alaninol

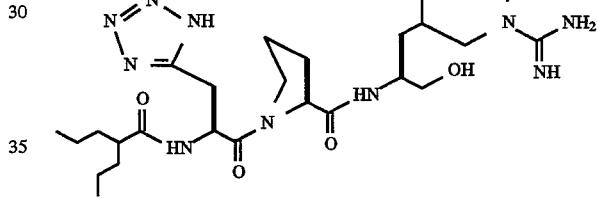

The compound of Example 17 (530 mg, 0.64 mmole) was subjected to catalytic hydrogenation in methanol (30 mL) and acetic acid in the presence of 10% palladium on carbon (50 mg) at 35 psi for 1.5 hours. The catalyst was filtered off and the filtrate concentrated to an oil (315 mg, 88%). Fast atom bombardment mass spectrometry confirmed the theoretical molecular weight of 562.

Example 19

Preparation of alpha-N-(2-propylpentanoyl-L-alanyl-(beta-tetrazol-5-yl)-prolyl-3-[3-piperidyl-(N-guanidino)]-L-alaninal.

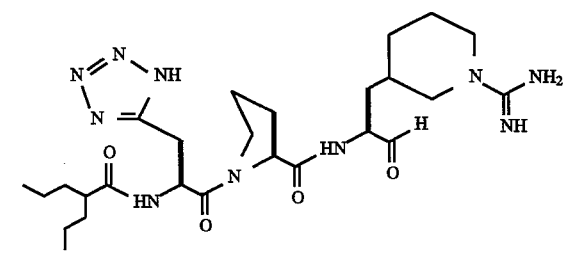

To a chilled solution of the compound of Example 18 (267 mg, 0.43 mmole) in dimethylsulfoxide and toluene (6 mL each), dichloroacetic acid (196 mL, 2.4 mmole) was added, followed by EDC (0.9 g, 4.7 mmole). The reaction was stirred for 5 minutes at 0° C. and 90 minutes at ambient temperature, and was quenched by addition of 50 mL water. The water layer was extracted twice with diethyl ether (10 mL portions), diluted to 100 mL with water and subjected to HPLC purification using a 20×250 mm reverse phase column containing a C-18 resin comprised of a 10 micron-size gel particles with a 300 angstrom pore size, eluting with a gradient ranging from 15–25% acetonitrile in water (containing 0.1% trifluoroacetic acid). The faster-moving diastereomer had a retention time of 15.5 minutes (referred to as isomer "19A") and the slower-moving diastereomer had a retention time of 17 minutes (referred to as isomer "19B"). Fast atom bombardment mass spectrometry confirmed the theoretical molecular weight of 560 for both diastereomers.

Example 20

Preparation semicarbazid-4-yl diphenylmethane, trifluoroacetate salt

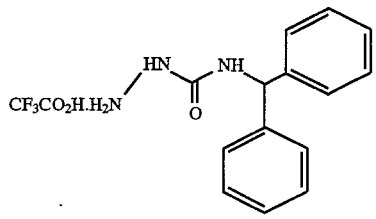

Step 1:

A solution of carbonyldiimidazole (16.2 g, 0.10 mole) in 225 mL of dimethylformamide was prepared at room temperature and allowed to stir under nitrogen. A solution of t-butyl carbazate (13.2 g, 0.100 moles) in 225 mL dimethylformamide was then added dropwise over a 30 minute period. Next, diphenylmethylamine (18.3 g, 0.10 moles) was added over a 30 minute period. The reaction was allowed to stir at room temperature under nitrogen for one hour. Water (10 mL) was added and this mixture was concentrated to about 150 mL under vacuum. This solution was poured into 500 mL water and extracted with 400 mL of ethyl acetate. The ethyl acetate phase was extracted two times each with 75 mL 1N HCl, water, saturated sodium bicarbonate and brine, and then was dried with anhydrous magnesium sulfate. The mixture was filtered and the solution was concentrated to give 29.5 g (85% yield) of 1-t-butoxycarbonyl-semicarbazid-4-yl diphenylmethane as a white foam. This material may be purified by recrystallization from ethyl acetate/hexane, but was pure enough to use directly in step 2: mp 142°–143° C. $^1$H NMR (CDCL$_3$) delta 1.45 (s, 9H), 6.10 (dd, 2H), 6.42 (s, 1H), 6.67 (bs, 1H), 7.21–7.31 (m, 10H). Anal. Calc'd. for C$_{19}$H$_{23}$N$_3$O$_3$: C, 66.84; H, 6.79; N, 12.31. Found: C, 66.46; H, 6.75; N; 12.90.

Step 2:

A solution of 3.43 g (10 mmole) of 1-t-butoxycarbonyl-semicarbazid-4-yl diphenylmethane in 12.5 mL of dichloromethane was treated with 12.5 mL of trifluoroacetic acid at 0° C. The reaction mixture was allowed to stir for 30 minutes at this temperature. The reaction mixture was then added dropwise to 75 mL of diethyl ether to give a precipitate. The resulting precipitate was filtered off and washed with diethyl ether to give 2.7 g (80% yield) of the title compound; mp 182°–184° C.

Example 21

Preparation of 3-thioamidobenzyl-N-acetylaminomalonic acid diethyl ester

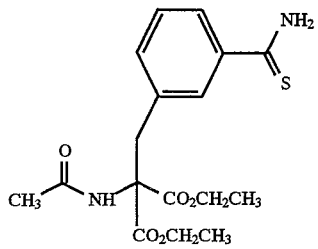

To a stirred solution of alpha-bromo-meta-tolunitrile (45.0 g, 0.24 mole), diethyl acetamidomalonate (48.0 g, 0.22 mole) and potassium iodide ((3.0 g, 0.018 mole) in dioxane (500 mL) was added 2.5M sodium ethoxide in ethanol (100 mL) dropwise under an argon atmosphere. After the addition was complete, the solution was refluxed for 6 hours. The reaction mixture was allowed to stand overnight at room temperature, then diluted with brine (250 mL) and water (250 mL), and extracted with ethyl acetate four times (1.0 L total). The combined extracts were washed with water (100 mL), 10% citric acid (100 mL), water (100 mL) and brine (2×50 mL), then dried over anhydrous magnesium sulfate and filtered; the solvent was removed under vacuum. The crude residue was recrystallized from ethyl acetate and diethyl ether in two crops to yield 43.51 g (60%) of the 3-cyanobenzyl-N-acetylaminomalonic acid diethyl ester as yellow crystals.

H$_2$S(g) was bubbled into a rapidly stirring solution of 3-cyanobenzyl-N-acetylaminomalonic acid diethyl ester (44.3 g, 0.13 mmole) in pyridine (300 mL) and triethylamine (100 mL) for 40 minutes. The reaction mixture was stirred at room temperature for 16 hours, then poured into 3.0 L of water. A yellow precipitate formed immediately. The solution was allowed to stand at 4° C. for 4 hours, then was filtered. The crude title compound was recrystallized from ethyl acetate and hexanes to yield 48.1 g (98%) of the title compound as yellow crystals. m.p. 183°–186° C. $^1$H NMR (CDCl$_3$): delta 1.31 (t, J=7.1 Hz, 6H), 2.06 (s, 3H), 3.70 (s, 2H), 4.29 (q, J=7.1 Hz, 4H), 4.80–4.87 (m, 1H), 6.60 (s, 1H), 7.10–7.20 (m, 1H), 7.27–7.35 (m, 2H), 7.60–7.70 (m, 2H). Anal. Calc'd for C$_{17}$H$_{22}$N$_2$O$_5$S: C, 55.72; H, 6.05; N, 7.64. Found: C, 55.55; H, 5.96; N, 7.76.

Example 22

Preparation of 3-amidino-D,L-phenylalanine, dihydrochloride salt

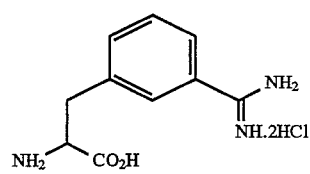

The compound of Example 21 (48.1 g, 0.13 mmole) was dissolved in acetone (800 mL). Iodomethane (18.3 mL, 0.19 mole, 1.5 equivalents) was added, and the solution was refluxed for 30 minutes. The solution was cooled to room temperature, and the intermediate thioimidate was filtered, dried and dissolved in methanol (500 mL). Ammonium acetate (14.8 g, 0.19 mole, 2 equivalents) was added. The reaction mixture was refluxed for 1 hour, then cooled to room temperature, and poured into ether (1.2 L). The solution was allowed to stand at 4° C. for 72 hours. The crude 3-amidinobenzyl-N-acetylaminomalonic acid diethyl ester was filtered, washed with ether, air dried, and then refluxed in concentrated HCl (250 mL) for 3 hours. The reaction mixture was concentrated under vacuum, diluted with water (0.5 L), and concentrated under vacuum again. These steps were repeated. The crude title compound was purified by cation-exchange (Sephadex SP-C25) using a gradient of 0–1.0N HCl as eluent to yield 10.8 g (30%) of the title compound as an off-white solid. $^1$H NMR (D$_2$O): delta 3.14–3.29 (2H, m), 4.17 (dd, J=7.4, 6.2 Hz, 1H), 7.42–7.69 (4H, m). Anal. Calc'd for $C_{10}H_{13}N_3O_2 \cdot 2HCl \cdot 1.9H_2O$: C, 38.20; H, 6.03; N, 13.36. Found: C, 38.51; H, 5.64; N, 12.89.

Example 23

Preparation of N-alpha-Boc-N-ω-4-methoxy-2,3,6-trimethylbenzenesulfonyl-3-amidino-D,L-phenylalanine

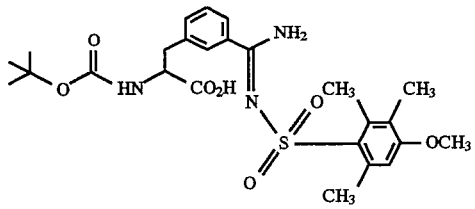

3-amidino-D,L-phenylalanine (4.00 g, 13 mmole) was dissolved in 50% aqueous dioxane (20 mL). Sodium bicarbonate (3.38 g, 40 mmole) was added, followed by di-t-butyl dicarbonate (2.93 g, 13 mmole) in dioxane (4 mL). The reaction mixture was stirred for 18 hours at room temperature. The solution was cooled in an ice bath, and 4.0N sodium hydroxide was added dropwise until the solution was pH 12. 4-methoxy-2,3,6-trimethylbenzenesulfonyl chloride (8.01 g, 32 mmole) in dioxane (10 mL) was added dropwise. 4.0N sodium hydroxide was added as needed to keep the pH at 12. The ice bath was removed. After 1 hour, 1.0N HCl was added to bring the solution to pH 7–8. The solution was diluted with an additional 50 mL of water and then was washed with ethyl acetate two times (20 mL each). The aqueous layer was acidified to pH 1.0 with 1.0N HCl and extracted with ethyl acetate three times (100 mL total). The combined white foam. A 30 mg sample of the title compound was further purified by preparative thin-layer chromatograph developing with 1% acetic acid/5% isopropanol/dichloromethane to give 9 mg of the title compound in a purer form. Rf=0.16 (1% acetic acid/5% isopropanol/dichloromethane). $^1$H NMR (CD$_3$OD): delta 1.32 (s, 9H), 2.14 (s, 3H), 2.63 (s, 3H), 2.71 (s, 3H), 2.93 (dd, J=13.7, 9.3 Hz, 1H), 3.22 (dd, J=13.7, 4.3 Hz, 1H), 3.85 (s, 3H), 4.34–4.37 (m, 1H), 6.72 (s, 1H), 7.35–7.47 (2H, m), 7.69–7.75 (m, 2H).

Example 24

Preparation of N-alpha-Boc-N-ω-4-methoxy-2,3,6-trimethytbenzenesulfonyl-3-amidino-D,L-phenylalanine-N-methyl-O-methyl-carboxamide

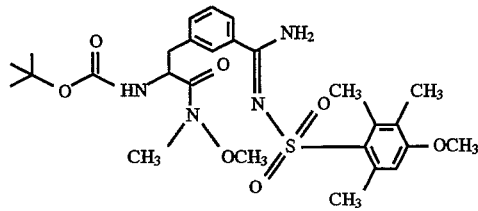

To a stirred solution of compound of Example 23 (1.00 g, 1.92 mmole), O,N-dimethyl hydroxylamine hydrochloride (375 mg, 3.85 mmole), hydroxybenzotriazole hydrate (294 mg, 1.92 mmole) and 4-methylmorpholine (1.06 mL, 9.62 mmole) in tetrahydrofuran (4 mL), cooled in an ice bath, was added EDC (406 mg, 2.12 mmole). The ice bath was removed, and the reaction mixture was stirred for 2 hours at room temperature. The reaction mixture was diluted with ethyl acetate (75 mL), washed with water, 10% citric acid, water, saturated sodium bicarbonate, and brine. The organic layer was dried over anhydrous magnesium sulfate and the solvent was removed under vacuum. 750 mg (69%) of the title compound was isolated. $^1$H NMR (CDCl$_3$): delta 1.33 (s, 9H), 2.14 (s, 3H), 2.66 (s, 3H), 2.75 (s, 3H), 2.80–2.88 (m, 1H), 3.06–3.20 (m, 4H), 3.70 (s, 3H), 3.84 (s, 3H), 4.98–5.06 (m, 1H), 5.21 (d, J=8.7 Hz, 1H), 6.48 (bs, 1H), 6.58 (s, 1H), 7.30–7.34 (m, 2H) 7.60–7.68 (m, 2H), 8.11 (bs, 1H). Anal. Calc'd for $C_{27}H_{38}N_4O_7S \cdot 0.5$ H$_2$O: C, 56.73; H, 6.88; N, 9.80. Found: C, 56.97; H, 6.66; N, 9.43.

Example 25

Preparation of N-alpha-Boc-N-ω-4-methoxy-2,3,6-trimethylbenzenesulfonyl-D,L-3-amidinophenylalaninal

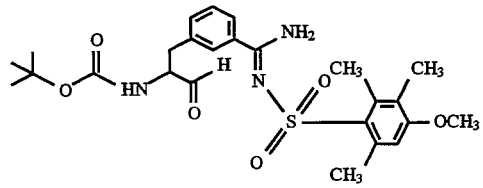

To a stirred solution of LiAlH$_4$ (2.00 mL of a 1.0 M solution in tetrahydrofuran, 1.24 mmole) in tetrahydrofuran (8 mL), cooled in a dry ice/acetone bath, the compound of Example 24 (0.75 g, 1.9 mmole in tetrahydrofuran (5 mL)) was added dropwise. The cooling bath was removed and the reaction mixture was allowed to warm to 5° C. The reaction mixture was re-cooled in the dry ice acetone bath and quenched with 3.0 mL of a 1:2.7 wt./wt. solution of potassium bisulfate in water. The reaction mixture was allowed to warm to room temperature, stirred for 3 hours, filtered and concentrated under vacuum. The residue was dissolved in ethyl acetate (20 mL), and washed with 10% citric acid (2 mL), water (2 mL), saturated sodium bicarbonate (2 mL) and brine (2 mL). The organic layer was dried over anhydrous magnesium sulfate and the solvent was removed under vacuum to yield 580 mg (86%) of the title compound. $^1$H NMR (CDCl$_3$): delta 1.31 (s, 9H), 2.07 (s, 3H), 2.57 (s, 3H), 2.67 (s, 3H), 2.90–3.17 (2H, m), 3.77 (s, 3H), 4.33–4.40 (1H, m), 5.02–5.08 (1H, m), 6.48 (1H, s), 7.23–7.31 (2H, m), 7.50–7.62 (2H, m), 7.94, (1H, bs), 8.05 (1H, bs), 9.55 (1H, s). Anal. Calc'd for $C_{25}H_{33}N_3O_6S \cdot 0.5H_2O$: C, 58.58; H, 6.69; N, 8.20. Found: C, 58.57; H, 6.72; N, 7.98.

Example 26

Preparation of N-alpha-Boc-N-ω-4-methoxy-2,3,6-trimethylbenzenesulfonyl-D,L-3-amidinophenylalaninal-semicarbazonyl-4-N-diphenylmethane

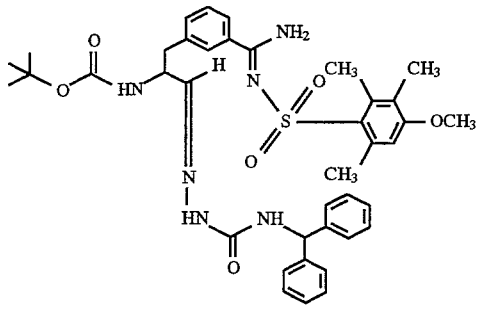

The compound of Example 25 (0.58 g, 1.9 mmole), the compound of example 20 (410 mg, 1.15 mmole) and sodium acetate trihydrate (188 mg, 1.38 mmole) were refluxed in 75% aqueous ethanol (10 mL) for 1 hour. After the reaction mixture was cooled to room temperature, it was diluted with ethyl acetate (50 mL), washed with 1.0N HCl (5 mL), water (5 mL), saturated sodium bicarbonate (5 mL) and brine (2×5 mL), and dried over anhydrous magnesium sulfate. The solvent was removed under vacuum to yield 750 mg (89% yield) of the title compound as an off-white foam. Analysis calculated for $C_{39}H_{46}N_6O_6S \cdot 1.0H_2O$: C, 62.88; H, 6.49; N, 11.28. Found: C, 63.14; H, 6.35 N, 11.10.

Example 27

Preparation of N-ω-4-methoxy-2,3,6-trimethylbenzene sulfonyl-D,L-3-amidinophenylalaninal-semicarbazonyl-4-N-diphenylmethane, trifluoroacetate salt

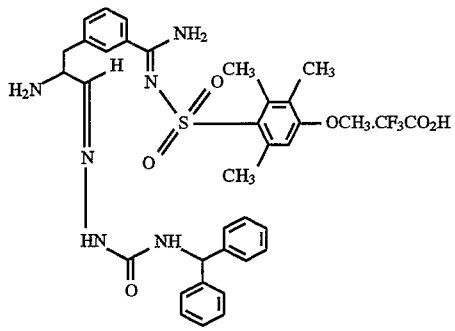

The compound of Example 26 (750 mg. 1.9 mmole) was treated with 50% trifluoroacetic acid/dichloromethane (3 mL) for 30 minutes at room temperature. The reaction mixture was added dropwise to ether (50 mL). The solution was allowed to stand at 4° C. for 18 hours. The product was filtered, and dried under vacuum to yield 600 mg (79% yield) of the title compound as an off-white solid. Analysis calculated for $C_{39}H_{46}N_6O_6S \cdot 1.3CF_3CO_2H$: C, 56.72; H, 5.11; N, 10.84. Found: C, 56.34; H, 5.47; N, 11.49.

Example 28

Preparation of N-(2-propylpentanoyl)-L-aspartyl-(beta-methyl ester)-L-prolyl-D,L-N-ω-4-methoxy-2,3,6-trimethylbenzenesulfonyl-D,L-3-amidinophenylalaninal-semicarbazonyl-4-N-diphenylmethane

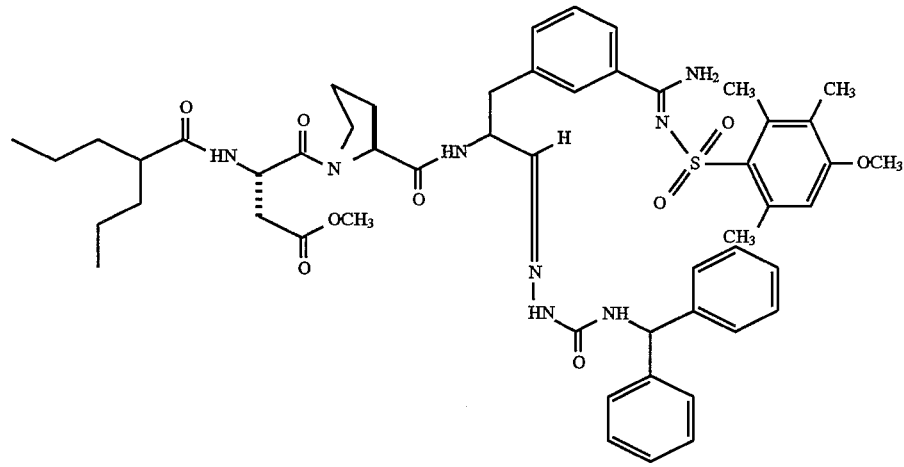

EDC (94 mg, 0.94 mmole) is added in one portion to a stirred solution of the compound of Example 3 (180 mg, 0.49 mmole), hydroxybenzotriazole (75 mg, 0.49 mmole), and 4-methylmorpholine (0.24 mL, 2.2 mmole) in dimethylformamide (5 mL) with cooling in an ice bath. After 30 minutes, the compound of Example 27 (360 mg, 0.49 mmole) is added. After an additional 2 hours, the reaction mixture is diluted with water (25 mL) and brine (25 mL). The product is filtered and dissolved into ethyl acetate (25 mL). The solution is washed with 10% citric acid, water, saturated sodium bicarbonate and brine, and is dried over anhydrous magnesium sulfate. The solvent is removed under vacuum. The resulting residue is chromatographed by flash chromatography on silica gel to give the title compound.

Example 29

Preparation of 2-propylpentanoyl-L-aspartyl-(beta-methyl ester)-L-prolyl-D, L-3-amidinophenylalaninal semicarbazone

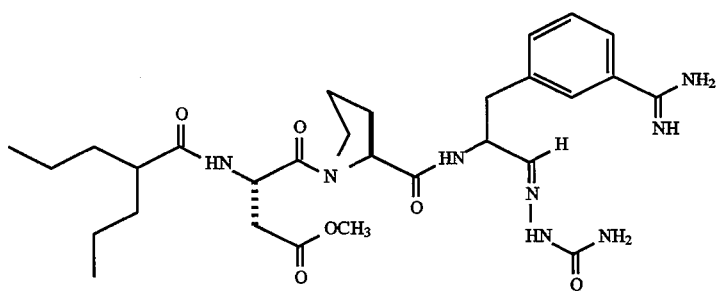

The compound of Example 28 (100 mg) is treated with hydrofluoric acid/anisole (9:1) for 30 minutes at −20° C. and 0° C. for 30 minutes. After removal of the hydrofluoric acid, the resulting residue is dissolved in 20% aqueous acetic acid and washed with diethyl ether. The aqueous layer is lyophilized to a powder, then is purified by preparative HPLC (C-18, eluting with 10–40% acetonitrile-water gradient containing 0.1% trifluoroacetic acid) to give the title compound.

Example 30

Preparation of 2-propylpentanoyl-L-aspartyl-(beta-methyl ester)-L-prolyl-D,L-3-amidinophenylalaninal

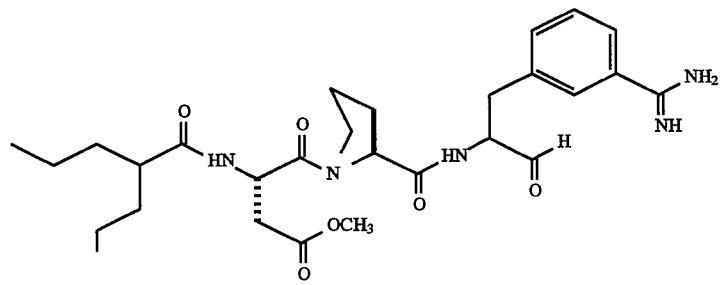

The compound of Example 29 (17 mg, 32 micromole) is dissolved in methanol (1 mL) and 1% aqueous trifluoroacetic acid (5 mL), then formalin (0.23 mL) is added. After 40 minutes, the solution is filtered through a 2 micron filter, diluted to a volume of 15 mL with water, and then is purified by preparative HPLC (C-18, eluting with 10–40% acetonitrile-water gradient containing 0.1% trifluoroacetic acid). The fractions containing the title compound are pooled and lyophilized to give the title compound.

Example 31

N-(4-methylbenzenesulfonyl)-L-aspartyl-(beta-methyl ester)-L-proline-O-benzyl ester

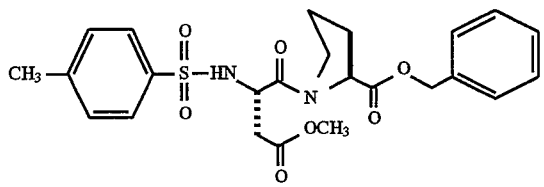

To a solution of the compound of Example 1 (112.6 g, 0.259 mole) and 400 mL of ethyl acetate at 0° C. is added with stirring 700 mL of ethyl acetate saturated with HCl(g). After about 1 hour, the solvent is removed under vacuum. The resulting solid is suspended in 500 mL of ethyl acetate to give a solution of L-aspartyl-(beta-methyl ester)-L-proline-O-benzyl ester hydrochloride salt.

To a chilled solution of the salt in acetonitrile (300 ml) is added triethylamine (144 ml, 1.04 mole) followed by 4-methylbenzene sulfonyl chloride (98.7 g, 0.518 mole). The ice bath is removed after 30 minutes and the reaction mixture is allowed to warm to 25° C. After about 12 hours, the reaction solvent is removed under vacuum and the remaining residue is picked up in ethylacetate. The organic phase is washed three times each with 1N HCl (3×100 mL), saturated sodium bicarbonate (3×100 mL) and brine (100 mL). The organic phase is dried over anhydrous magnesium sulfate, filtered and the solvent is removed under vacuum to give the desired compound.

Example 32

N-(4-methylbenzenesulfonyl)-L-aspartyl-(beta-methyl ester)-L-proline

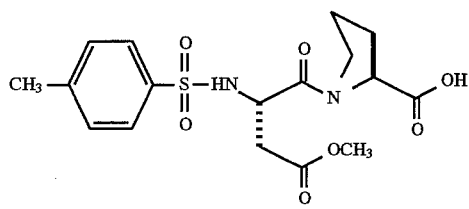

To a mixture of the compound of Example 31 (111.6 g, 0.228 mole), 500 mL of methanol and 11 g of 10% palladium on carbon (wet with dichloromethane) is added hydrogen gas via a balloon. The reaction mixture is stirred overnight at 25° C. The following day, the solution is filtered through celite and the celite is washed with dichloromethane (200 mL). The flitrates are combined and the organic solvent is evaporated under vacuum. The resulting solid is triturated with 300 mL of diethyl ether, filtered and dried to yield the title compound.

Example 33

Preparation of alpha-N-(4-methylbenzenesulfonyl)-aspartyl (beta-methyl ester/-prolyl-3-[3-piperidyl-(N-guanidino(bis-benzyloxycarbonyl))]-L-alaninol

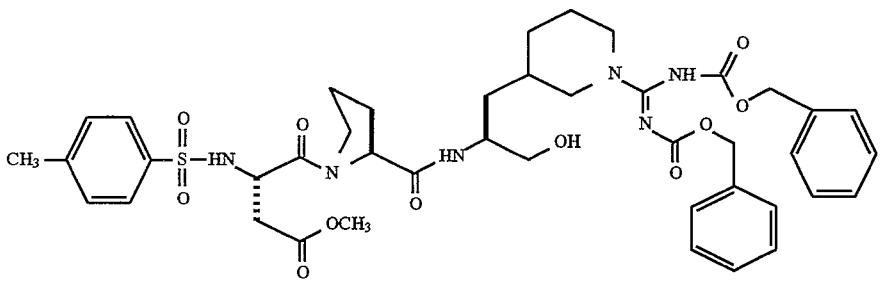

To a suspension of the compound of Example 8 (2.06 g, 4.08 mmole) in acetonitrile (22 mL) is added successively the compound of Example 32 (2.21 g, 5.56 mmole), EDC (1.12 g, 5.84 mmole), 1-hydroxybenzotriazole hydrate (979 mg, 6.39 mmole), and N-methylmorpholine (3 mL, 27.80 mmole). The solution is stirred at ambient temperature for twelve hours. The solvent is removed under vacuum and the resulting residue is picked up in a 9:1 mixture of dichloromethane/isopropanol (40 mL) and washed two times each with 15 mL portions of 1N sodium bisulfate, saturated sodium bicarbonate and saturated sodium chloride. The organic layer is dried over anhydrous sodium sulfate and concentrated under vacuum to yield the title compound.

Example 34

Preparation of alpha-N-(4-methylbenzenesulfonyl)-aspartyl (beta-methyl ester)-prolyl-3-[3-piperidyl-(N-guanidino)]-L-alaninol

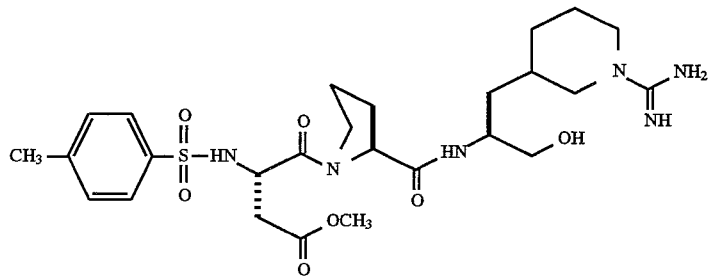

The compound of Example 33 (1.91 g, 2.25 mmole) is subjected to catalytic hydrogenation in methanol (100 mL) and acetic acid (10 mL) in the presence of 10% palladium on carbon (185 mg) at 30 psi for 2.5 hours. The catalyst is filtered. The filtrate after concentration under vacuum yields the title compound as a mixture of two diastereomers.

Example 35

Preparation of alpha-N-(4-methylbenzenesulfonyl)-aspartyl (beta-methyl ester)-prolyl-3-[3-piperidyl-(N-guanidino)]-L-alaninal

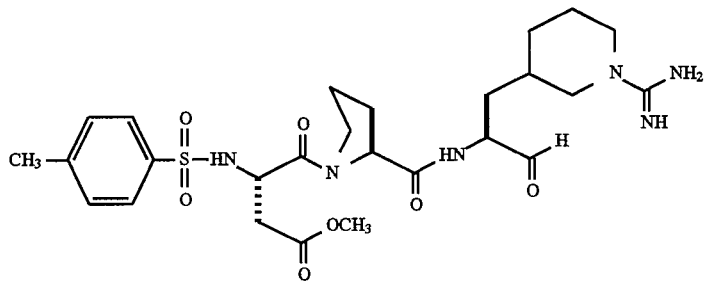

To a chilled solution of the compound of Example 34 (0.81 g, 1.4 mmole) in dimethylsulfoxide and toluene (15 mL each) is added dichloroacetic acid (567 mL, 6.9 mmole) followed by EDC (2.68 g, 14 mmole) at one minute later. The reaction is stirred for 5 minutes at 0° C., 85 minutes at ambient temperature, and then is quenched with 60 mL water. The water layer is extracted twice with diethyl ether (10 mL portions) and subjected to HPLC using a 47×300 mm reverse phase column containing a C-18 resin comprised of 10 micron-size gel particles with a 300 angstrom pore size. The column is eluted with a gradient ranging from 15% to 30% acetonitrile in water (containing 0.1% trifluoroacetic acid). The HPLC fractions will yield fast moving and slow moving peaks containing the two diastereomers of the title compound. The fractions containing each diasteromer when pooled then lyophilized will give the two diasteromers of the title compound.

Example A

Kinetic Analysis of 2-PrPent-Asp(OMe)-Pro-Ala(3-guanPip)-al (Isomer B) in an in vitro Thrombin Inhibition Assay The ability of the compound of Example 11, 2-PrPent-Asp(OMe)-Pro-Ala(3-guanPip)-al, isomer 11B, (hereinafter referred to Isomer B), of the present invention to act an inhibitor of thrombin catalytic activity was assessed by determining the inhibition constant, Ki.

Enzyme activity was determined using the chromogenic substrate Pefachrome t-PA ($CH_3SO_2$-D-hexahydrotyrosine-glycyl-L-arginine-p-nitroanilide), obtained from Pentapharm Ltd. The substrate was reconstituted in deionized water prior to use. Purified human alpha-thrombin (3000 U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for the Ki determination was conducted by combining in appropriate wells of a Corning microtiter plate, 50 microliters of HBSA, 50 microliters of Isomer B at a specified concentration diluted in HBSA (or HBSA alone for $V_{O\ (uninhibited\ velocity)}$ measurement), and 50 microliters of the chromogenic substrate (250 micromolar, 5-times Km) At time zero, 50 microliters of alpha-thrombin diluted in HBSA, was added to the wells yielding a final concentration of 0.5 nM in a total volume of 200 microliters. Velocities of chromogenic substrate hydrolysis which occurred over 40 minutes was measured by the change in absorbance at 405 nm using a Thermo Max® Kinetic Microplate Reader. The Ki value for 2-PrPent-Asp(OMe)-Pro-Ala(3-guanPip)-al (Isomer 11B) was determined using the relationships developed by Williams and Morrison, Methods in Enzymology, 63: 437 (1979) using steady state velocities (Vs) measured over 40 minutes. The extent of substrate hydrolysis was less than 5% over the course of this assay. Table 1 below gives the Ki value for Isomer B described in this patent. The data shows the utility of this compound as a potent in vitro inhibitor of human alpha-thrombin.

TABLE 1

| Inhibitor Constant (Ki) of Isomer B against human alpha-thrombin amidolytic activity. ||
|---|---|
| Compound | Ki (nM)* |
| Isomer B | 0.381 ± 52 |

*Mean ± SD, n = 3

Example B

In vitro Enzyme Assays for Specificity Determination

Illustrative of the selectivity of the compounds of the present invention, the ability of Isomer B to act as a selective inhibitor of thrombin catalytic activity was assessed by determining the concentration of this compound which inhibited the activity of this enzyme by 50%, ($IC_{50}$), and comparing this value to that determined for the following related serine proteases: recombinant tissue plasminogen activator (rt-PA), plasmin, activated protein C, chymotrypsin, and trypsin.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a corning microtiter plate, 50 microliters of HBSA, 50 microliters of Isomer B at a specified concentration (covering a broad concentration range) diluted in HBSA (or HBSA alone for $V_o$ (uninhibited velocity) measurement), and 50 microliters of the enzyme diluted in HBSA. Following a 30 minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value for Isomer B.

Thrombin Assay

Thrombin catalytic activity was determined using the chromogenic substrate Pefachrome t-PA ($CH_3SO_2$-D- hexahydrotyrosine-glycyl-L-arginine-p-nitroanilide, obtained from Pentapharm Ltd.). The substrate was made up in deionized water followed by dilution in HBSA prior to the assay in which the final concentration was 300 micromolar (about 5-times Km). Purified human alpha-thrombin was obtained from Enzyme Research Laboratories, Inc. The enzyme was diluted into HBSA prior to the assay in which the final concentration was 0.25 nM.

Recombinant tissue plasminogen activator (rt-PA)

rt-PA catalytic activity was determined using the substrate, Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 500 micromolar (about 3-times Km). Recombinant human t-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2251 [D-valyl-L-leucyl-L-lysine-p-nitroanilide], which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC)

aPC catalytic activity was determined using the chromogenic substrate, Pefachrome PC (delta-carbobenzloxy-D-lysine-L-prolyl-L-arginine-p-nitroanilide), obtained from Pentapharm Ltd.). The substrate was made up in deionized water followed by dilution in HBSA prior to the assay in which the final concentration was 250 micromolar (about 3-5 times Km). Purified human aPC was obtained from Hematologic Technologies, Inc. The enzyme was diluted into HBSA prior to assay in which the final concentration was 1.0 nM.

Chymotrypsin

Chymotrypsin catalytic activity was determined using the chromogenic substrate, S-2586 (methoxy-succinyl-L-arginine-L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3X-crystallized;CDI) bovine pancreatic alpha-chymotrypsin was obtained from Worthington Biochemical Corp. The enzyme was reconstituted in deionized water and diluted into HBSA prior to assay in which the final concentration was 1.0 nM.

Trypsin

Trypsin catalytic activity was determined using the chromogenic substrate, S-2222 (benzoyl-L-isoleucine-L-glutamic acid-[gamma-methyl ester]-L-arginine-p-nitroanilide), which was obtained from Kabi Diagnostica. The substrate was made up in deionized water followed by dilution in HBSA prior to the assay in which the final concentration was 250 micromolar (about 4-times Km). Purified (3X-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table 2 lists the determined $IC_{50}$ values for Isomer B against the enzymes listed above and demonstrates the high degree of specificity of this compound for the inhibition of alpha-thrombin compared to these related serine proteases.

TABLE 2

$IC_{50}$ values for the inhibition of thrombin amidolytic activity compared to selected serine proteases for Isomer B.

| Enzyme | $IC_{50}$ (nM) Isomer B |
| --- | --- |
| alpha-thrombin | 1.5 |
| rt-PA | NI* |
| plasmin | NI* |
| aPC | NI* |
| chymotrypsin | NI* |
| trypsin | 201 |

Figure 3:
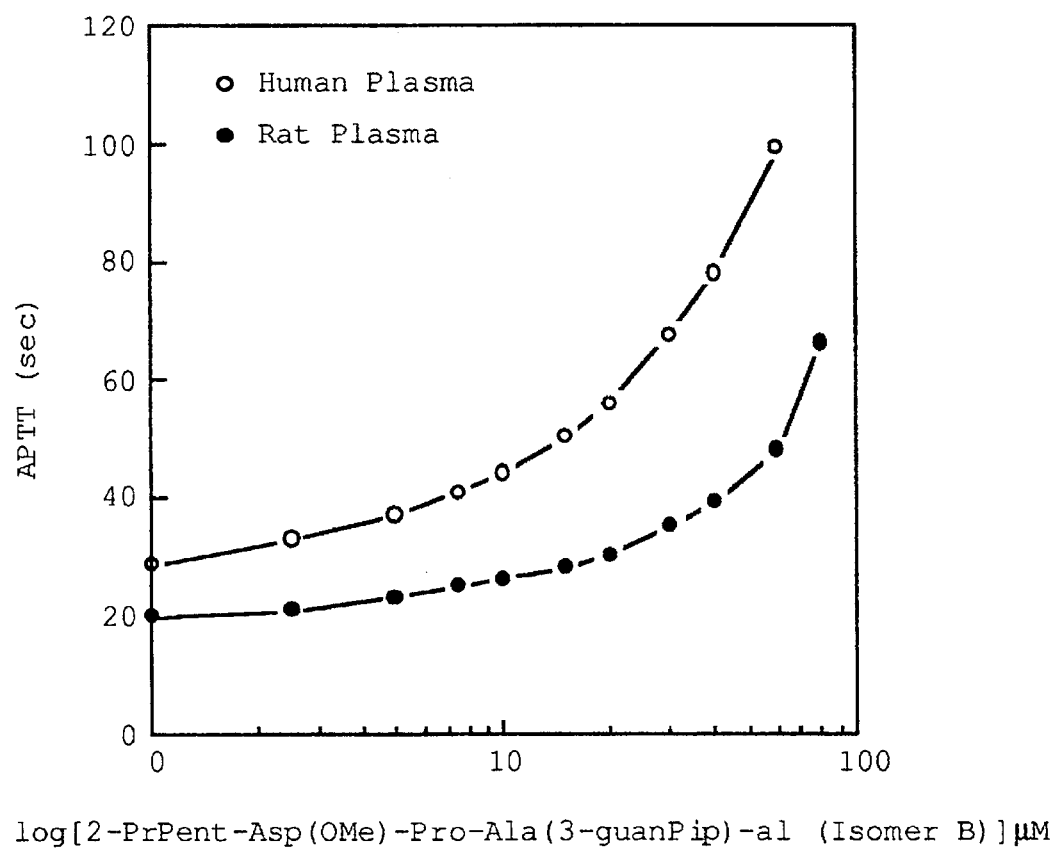
FIG. 3 depicts the anticoagulant effect of the compound of Example 11, 2-PrPent-Asp(OMe)-Pro-Ala(3-guanPip)-al (Isomer 11B), referred to as Isomer B, measured in citrated rat (●) and human (○) plasma using the activated partial thromboplastin time (APTT) assay. The control clotting times (0 inhibitor) for rat and human plasma were 20 seconds and 28 seconds, respectively. The concentration of Isomer B which caused a doubling of the control clotting time in rat and human plasma was 39 micromolar and 21 micromolar, respectively. The data represents the mean of two independent determinations.

*-No inhibition observed at the maximal concentration of inhibitor assayed- 2,500 nM Example C Ex vivo Anticoagulant Effects of Isomer B in Rat and Human Plasma The ex vivo anticoagulant effects of Isomer B was determined by measuring the prolongation of the activated partial thromboplastin time (APTT) over a broad concentration range of the added inhibitor, using pooled normal human and rat plasma. Fresh frozen citrated pooled normal human plasma was obtained from George King Biomedical, Overland Park, Kans. Pooled normal rat plasma was prepared from citrated whole blood collected from anesthetized rats using standard procedures. The plasma was flash frozen and stored at −80° C. until use. Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay was conducted by making a series of dilution's of the test compounds in rapidly thawed plasma followed by adding 200 microliters to the wells of the assay carousel. As shown in FIG. 3, Isomer B prolonged the APTT in a dose dependent manner in both rat and human plasma demonstrating an anticoagulant effect in both species of mammals.

Example D

Evaluation of the Antithrombotic Potential of Isomer B in an Experimental Rat Model of Thrombosis The demonstrated anticoagulant effects of Isomer B in both rat and human citrated plasma are predictive that this compound may have potent antithrombotic effects in vivo. The antithrombotic (prevention of thrombus formation) properties of Isomer B are evaluated using the following established experimental rat model of acute vascular thrombosis.

Rat model of $FeCl_3$-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of $FeCl_3$ absorbed to a piece of filter paper. The $FeCl_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl₃ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res.,60: 269–280 (1990).

Male Harlan Sprague Dawley rats (420–450 g) are acclimated at least 72 hours prior to use and fasted for 12 hours prior to surgery with free access to water. The animals are prepared, anesthetized with Nembutal followed by the insertion of catheters for blood pressure monitoring, drug and anesthesia delivery. The left carotid artery is isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals are randomized in either a control (saline) or treatment group with test compound, Isomer B, with at least 6 animals per group per dose. The test compound is administered as a single intravenous bolus using a wide range of doses following the placement of the flow probe and 5 minutes prior to the thrombogenic stimulus. At t=0, a 3 mm diameter piece of filter paper (Whatman #3) soaked with 10 microliters of a 35% solution of fresh FeCl₃ (made up in water) is applied the segment of isolated carotid artery distal to the flow probe. Blood pressure, blood flow, heart rate, and respiration are monitored for 60 minutes.

The incidence of occlusion (defined as the attainment of zero blood flow) is recorded as the primary end point and used as a measure of the antithrombotic efficacy of Isomer B.

The effective dose of Isomer B which prevents 50% of thrombotic occlusions in this model ($ED_{50}$) is determined from the above data by plotting the incidence of occlusion versus the dose administered. This will allow a direct comparison of the antithrombotic efficacy of isomer B with other antithrombotic agents, such as heparin, Argatroban and Hirulog™ which may also evaluated in this model as described above. Table 3 lists the $ED_{50}$ values for several well-known anticoagulant agents in this model which will be used to compared to Isomer B.

TABLE 3

Efficacy ($ED_{50}$) of clinically effective antithrombotic agents for the prevention of thrombus formation in the FeCl₃ model of arterial thrombosis.

| Compound | Ki[a] (nM) | $ED_{50}$[b] (mg/kg) |
|---|---|---|
| Standard Heparin |  | 300 U/kg |
| Argatroban | 19.0[c] | 3.8 mg/kg |
| Hirulog™ | 2.56[d] | 3.0 mg/kg |

[a]Ki determined using human alpha-thrombin as described above and in items c and d.
[b]$ED_{50}$ is defined as the dose that prevents the incidence of complete thrombotic occlusion in 50% of animals tested.
[c]Kikumoto, R. et. al. Biochemistry, 23: 85–90 (1984).
[d]Witting, J.I. et. al. Biochem. J., 283: 737–743 (1992).

$ED_{50}$ data for Isomer B when compared with such data for heparin, Argatroban and Hirulog™ will show the effectiveness of Isomer B in preventing occlusive thrombus formation in this experimental model. The relevance of this data to preventing human thrombosis can then be inferred from the comparison to the other anticoagulant agents which are evaluated in an identical manner in this experimental model and have demonstrated antithrombotic efficacy in preventing thrombus formation clinically, as described in the following literature citations: Heparin: Hirsh, J. N. Engl. J. Med., 324: 1565–1574 (1992), Cairns, J. A. et. al., Chest, 102: 456S–481S (1992); Argatroban: Gold, H. K. et.al., J. Am. Coll. Cardiol., 21: 1039–1047 (1993); and Hirulog™: Sharma, G.V.R.K. et.al., Am. J. Cardiol., 72: 1357–1360 (1993) and Lidón, R. M. et.al., Circulation, 88: 1495–150 (1993). The in vivo comparison of Isomer B with the clinically effective antithrombotic agents, Standard Heparin, Argatroban, and Hirulog™, in the same rodent model of experimental thrombosis coupled with the demonstrated anticoagulant effects of Isomer B in both rat and human plasma described above in Example C will show that Isomer B will be an effective antithrombotic agent in humans.

We claim:

1. A compound of the formula:

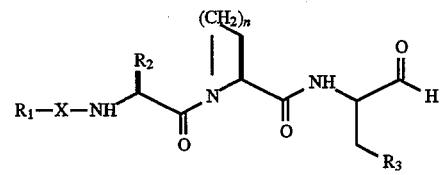

wherein (a) X is selected from the group consisting of —OC(=O)—, —NH—C(=O)—, —C(=O)—, —S(O)₂—, —NH—S(O)₂— and —N(R')—S(O)₂— wherein R' is alkyl of 1 to about 4 carbon atoms, aryl of about 6 to about 14 carbon atoms, or aralkyl of about 6 to about 15 carbon atoms;

(b) R₁ is selected from the group consisting of:
   (1) alkyl of about 3 to about 10 carbon atoms,
   (2) alkyl of 1 to about 3 carbon atoms substituted with cyclic alkyl of about 5 to about 8 carbon atoms,
   (3) alkenyl of about 3 to about 6 carbon atoms which is optionally substituted with cyclic alkyl of about 5 to about 8 carbon atoms,
   (4) aryl of about 6 to about 14 carbon atoms which is optionally mono-substituted with Y₁ or optionally di-substituted with Y₁ and Y₂,
   (5) aralkyl of about 6 to about 15 carbon atoms which is optionally mono-substituted in the aryl ring with Y₁ or optionally di-substituted in the aryl ring with Y₁ and Y₂,
   (6) aralkenyl of about 8 to about 15 carbon atoms which is optionally mono-substituted in the aryl ring with Y₁ or optionally di-substituted in the aryl ring with Y₁ and Y₂,

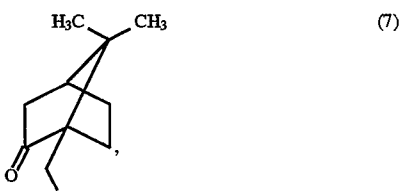
(7)

-continued

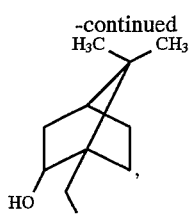
(8)

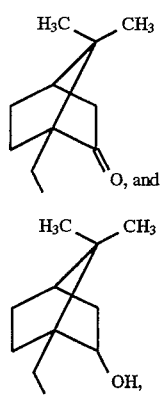
(9)

(10)

wherein $Y_1$ and $Y_2$ are independently selected from the group consisting of —$Z_1$, —$OZ_1$, —OH, —$S(O)_mZ_1$, —$S(O)_3H$, —C(O)OH, —C(O)O$Z_1$, —P(O)$_3$H, and tetrazolyl where m is 0, 1 or 2 and $Z_1$ is alkyl of 1 to about 12 carbon atoms, aryl of about 6 to about 14 carbon atoms and an aralkyl of about 6 to about 15 carbon atoms;

(c) $R_2$ is selected from the group consisting of

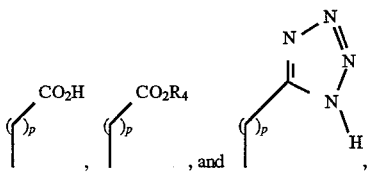

wherein p is 1 or 2 and $R_4$ is selected from the group consisting of alkyl of 1 to about 4 carbon groups, aryl of about 6 to about 15 carbon atoms;

(d) n is 1, 2 or 3;

(e) $R_3$ is

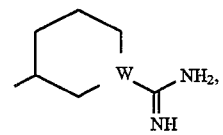

where W is nitrogen and pharmaceutically acceptable salts thereof.

2. A compound according to claim 1 wherein X is —C(=O)— or —S(O)$_2$—.

3. A compound according to claim 2 wherein $R_1$ is alkyl of 3 to 10 carbon atoms or aralkyl.

4. A compound according to claim 3 wherein n is 1 or 2.

5. A compound according to claim 4 wherein p is 1.

6. A compound according to claim 5 wherein n is 2.

7. A compound according to claim 6 wherein $R_1$ is branched chain alkyl of 4 to 10 carbon atoms.

8. A compound according to claim 7 wherein X is —C(=O)—.

9. A compound according to claim 8 wherein $R_2$ is

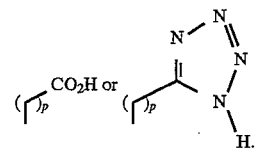

10. A compound according to claim 8 wherein $R_2$ is

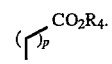

11. A compound according to claim 10 wherein $R_1$ is 4-heptyl and $R_4$ is methyl.

12. A compound according to claim 1 wherein n 1 or 2.

13. A compound according to claim 12 wherein n is 2.

14. A compound according to claim 13 wherein $R_1$ is alkyl of 3 to 10 carbon atoms or aralkyl.

15. A compound according to claim 14 wherein p is 1.

16. A compound according to claim 1 wherein X is —C(=O)— or —S(O)2—, $R_1$ is branched chain alkyl of 4 to 10 carbon atoms, p is 1, and n is 2.

* * * * *